United States Patent [19]

Lesher

[11] 4,009,208

[45] Feb. 22, 1977

[54] N,N'-HEPTAMETHYLENEBIS(4-METHOXYBENZAMIDE)

[75] Inventor: George Y. Lesher, East Greenbush, N.Y.

[73] Assignee: Sterling Drug Inc., New York, N.Y.

[22] Filed: Nov. 21, 1972

[21] Appl. No.: 308,498

Related U.S. Application Data

[60] Division of Ser. No. 62,186, Aug. 7, 1970, abandoned, which is a continuation-in-part of Ser. No. 756,373, Aug. 30, 1968, abandoned.

[52] U.S. Cl. .............................. 260/559 R; 424/282
[51] Int. Cl.² ....................................... C07C 103/82
[58] Field of Search ................................ 260/559 R

[56] References Cited

UNITED STATES PATENTS 2,190,829   2/1940   Graves ............................... 260/559

Primary Examiner—Henry R. Jiles
Assistant Examiner—R. W. Ramsuer
Attorney, Agent, or Firm—Robert K. Bair; B. Woodrow Wyatt

[57] ABSTRACT

4-(Q-O)-4'-R₁-N,N'-alkylenebis(benzamides), N,N'-alkylenebis(3,4-methylenedioxybenzamides) or N,N'-alkylenebis[4-(lower-alkoxy)benzamides], having endocrinological properties, where Q is lower-alkyl, lower-alkoxyalkyl, lower-alkenyl, halo-lower-alkyl, halo-lower-alkenyl, lower-cycloalkyl, phenyl and BN-(lower-alkyl) where BN is di-(lower-alkyl)amino or a saturated N-heteromonocyclic radical having from five to seven ring atoms and alkylene has at least five carbon atoms between its two connecting linkages and R₁ is Q-O-, hydrogen, lower-alkoxy, lower-alkyl, halo, benzyloxy, hydroxy, di-(lower-alkyl)amino, nitro, amino or trihalomethyl are prepared preferably by reacting the appropriate diamine or N-(aminoalkyl)-benzamide with two or one molar equivalents, respectively, of the appropriate benzoyl halide.

1 Claim, No Drawings

N,N'-HEPTAMETHYLENEBIS(4-METHOXYBENZAMIDE)

This application is a division of my copending application Ser. No. 62,186, filed Aug. 7, 1970 and now abandoned, which in turn is a continuation-in-part of my copending application Ser. No. 756,373, filed Aug. 30, 1968 and now abandoned.

This invention relates to compositions of matter known in the art of chemistry as N,N'-alkylenebis(benzamides) and to their preparation.

The invention in its composition aspect resides in the compounds having the formula I, II or III

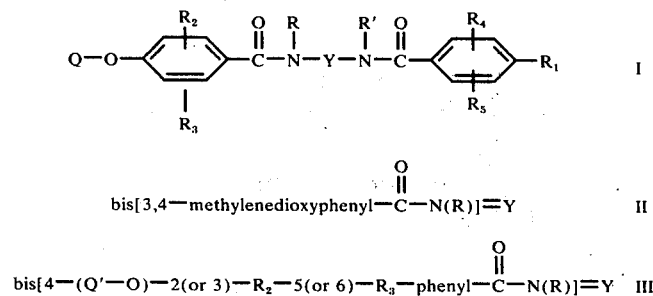

$$\text{bis}[3,4\text{—methylenedioxyphenyl}—\overset{O}{\overset{\|}{C}}—N(R)]=Y \quad\quad II$$

$$\text{bis}[4—(Q'—O)—2(\text{or }3)—R_2—5(\text{or }6)—R_3—\text{phenyl}—\overset{O}{\overset{\|}{C}}—N(R)]=Y \quad\quad III$$

where Q is lower-alkoxyalkyl, lower-alkenyl, halo-lower-alkyl, halo-lower-alkenyl, lower-cycloalkyl, phenyl and BN-(lower-alkyl) where BN is di-(lower-alkyl)amino or a saturated N-heteromonocyclic radical having from five to seven ring atoms; Q' is lower-alkyl; R and R' are each hydrogen or lower-alkyl or, in the case of formula I, lower-hydroxyalkyl or phenyl; $R_1$ is Q—O—, hydrogen, lower-alkoxy, lower-alkyl, halo, benzyloxy, hydroxy, di-(lower-alkyl)amino, nitro, amino or trihalomethyl; $R_2$, $R_3$, $R_4$ and $R_5$ are each hydrogen, lower-alkyl, lower-alkoxy, halo, benzyloxy or hydroxy; Y is alkylene having from five to twelve carbon atoms inclusive and having at least five carbon atoms between its two connecting linkages wherein a carbon atom of said alkylene more than two carbon atoms removed from the amide nitrogen atoms can be replaced by —O—, —S—, —S—S—, —Se—Se—, =SO, =$SO_2$, =NH, =N(lower-alkyl), =N(CO-phenyl-4-O-Q), =C=O, —CH=, CH—, —C≡C— or

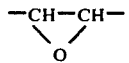

or where Y represents Y'—Z—Y'' where Y' is alkylene having from one to four carbon atoms inclusive; Y'' is a direct linkage or alkylene having from one to four carbon atoms inclusive, Z is phenylene or cycloalkylene having from three to six ring-carbon atoms inclusive.

The compounds of this composition aspect of the invention, when tested according to standard endocrinological evaluation procedures in animals, have been found to possess the inherent applied use characteristics of producing significant increases in adrenal weights in female rats, thereby indicating an inhibition of adrenal steroidogenesis. Such inhibition of adrenal steroidogenesis may be useful in the control of disease entities associated with adrenal hyperfunction. Members of the composition aspect of the invention also were found to be useful in having antifertility activity in female rats. The compounds of formula II were found to be useful in having hypocholesteremic activity in male rats.

"Lower-alkyl", as used herein is an alkyl radical, preferably having from one to six carbon atoms, which can be arranged as straight or branched chains including, for instance, but without limiting the generality of the foregoing, methyl, ethyl, n-propyl, isopropyl, sec-butyl, isobutyl and n-hexyl.

"Lower-alkoxy", as used herein is an alkoxy radical, preferably having from one to six carbon atoms, which can be arranged as straight or branched chains, including, for instance, but without limiting the generality of the foregoing, methoxy, ethoxy, n-propoxy, isopropoxy, sec-butoxy, isobutoxy and n-hexoxy.

"Di-(lower-alkyl)amino", as used herein is a dialkylamino radical, where each alkyl preferably has from one to six carbon atoms and can be arranged as straight or branched chains, di-(lower-alkyl)amino including, for instance, but without limiting the generality of the foregoing, dimethylamino, diethylamino, ethylmethylamino, di-n-propylamino, diisopropylamino, methyl-n-butylamino, diisobutylamino and di-n-hexylamino.

"Lower-hydroxyalkyl", as used herein is a hydroxyethyl radical, preferably having from two to six carbon atoms and having its free valence bond on a carbon atom other than that containing hydroxy, including, for instance, but without limiting the generality of the foregoing, 2-hydroxyethyl, 2-hydroxypropyl, 2-hydroxybutyl, 2-hydroxyhexyl, 3-hydroxypropyl, 4-hydroxybutyl, 6-hydroxyhexyl and 2-hydroxy-2-methylpropyl.

"Lower-alkoxyalkyl", as used herein is an alkoxyalkyl radical, preferably having from three to six carbon atoms, which can be arranged as straight or branched chains, illustrated by 2-methoxyethyl, 2-ethoxyethyl, 3-methoxypropyl, 4-methoxybutyl, 3-ethoxypropyl, 2-methoxypropyl, 3-isopropoxypropyl, 3-n-propoxypropyl, 5-methoxypentyl, and the like.

"Lower-alkenyl", as used herein is an alkenyl radical, preferably having from three to six carbon atoms, illustrated by 2-propenyl (allyl), 2-butenyl, 2-methyl-2-propenyl and 2-hexenyl.

"Halo-lower-alkyl", is an alkyl radical, preferably having from one to six carbon atoms and having from one to five halo substituents, i.e., fluoro, chloro, bromo and iodo, preferably fluoro and chloro, illustrated by chloromethyl, fluoromethyl, 2-chloroethyl, 2-fluoroethyl, dichloromethyl, difluoromethyl, dibromomethyl, diiodomethyl, trichloromethyl, trifluoromethyl, 2-chloro-1,1,2-trifluoroethyl, 2,2,2-trichloroethyl, 2,2,2-trifluoroethyl, 1,1,2,2,2-pentafluoroethyl, 1,1,2,2-tetrafluoro-n-butyl, 1,1,2-trifluoro-n-hexyl, 2,2,3,3,3-pentafluoropropyl, and the like.

"Halo-lower-alkenyl", as used herein is an alkenyl radical, preferably having from two to six carbon atoms

and from one to three halo substituents, i.e., fluoro, chloro, bromo and iodo, preferably fluoro and chloro, illustrated by —CH=CHCl, —CH=CCl$_2$, —CH=CHF, —CH=CF$_2$, —CF=CF$_2$, —CH$_2$CH=CHCl, —CH$_2$CH=CHF, —CH$_2$CH=CHBr, —CH$_2$CH=CHI, —CH$_2$C(Cl)=CHCl, —CH$_2$C(F)=CHF, —CH$_2$C(Cl)=CCl$_2$, —CH$_2$C(F)=CF$_2$, —CH$_2$CH$_2$CH=C(Cl)CH$_3$,
—CH$_2$CH$_2$C(Cl)=C(Cl)CH$_3$,
—CH$_2$CH$_2$C(F)=C(F)CH$_3$, —CH$_2$CH=CCl$_2$,
—CH$_2$CH=CF$_2$ and —CH$_2$CH$_2$CH$_2$CH=C(Cl)CH$_3$.

"Lower-cycloalkyl", as used herein is a cycloalkyl radical, preferably having from three to six carbon atoms, illustrated by cyclopropyl, cyclobutyl, cyclopentyl and cyclohexyl.

"Saturated N-heteromonocyclic", as used herein, e.g., as represented by BN in the definition of formula I, represents an N-heteromonocyclic radical having from five to seven ring atoms, illustrated by pyrrolidino, piperidino, morpholino, hexamethyleneimino, piperazino and lower-alkylated derivatives thereof where the lower-alkyl radicals can be attached to any available ring-atom and can vary preferably from one to three in number, e.g., 2-methylpiperidino, 3-ethylpiperidino, 4-methylpiperidino, 2,6-dimethylpiperidino, 2,4-dimethylpiperidino, 2,4,6-trimethylpiperidino, 3-n-propylpiperidino, 2,2-dimethylpiperidino, 2-methylpyrrolidino, 2,5-dimethylpyrrolidino, 2,3-dimethylmorpholino, 2-ethylmorpholino, 2-methylhexamethyleneimino, 2,7-dimethylhexamethyleneimino, 4-methylpiperazino, 3-ethylpiperazino and 2,4,6-trimethylpiperazino.

"Alkylene", as used herein, as designated by Y in formula I has from five to twelve carbon atoms and has at least five carbon atoms between its two connecting linkages, illustrated by —(CH)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—and —(CH$_2$)$_{12}$—. The alkylene radical Y when interrupted as defined above is illustrated by —CH$_2$CH$_2$OCH$_2$CH$_2$—, —CH$_2$CH$_2$OCH$_2$CH$_2$CH$_2$—, —CH$_2$CH$_2$SCH$_2$CH$_2$—, —CH$_2$CH$_2$CH$_2$SCH$_2$CH$_2$CH$_2$—, —CH$_2$CH$_2$-S-S-CH$_2$CH$_2$—, —CH$_2$CH$_2$—Se—Se—CH$_2$CH$_2$—,

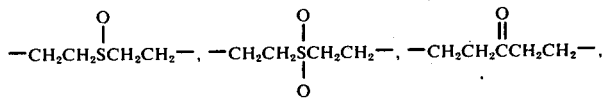

—CH$_2$CH$_2$CH=CHCH$_2$CH$_2$CH$_2$—,
—CH$_2$CH$_2$C CCH$_2$CH$_2$CH$_2$—, —CH$_2$CH$_2$NHCH$_2$CH$_2$—,

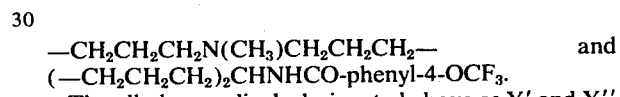

—CH$_2$CH$_2$CH$_2$N(CH$_3$)CH$_2$CH$_2$CH$_2$— and (—CH$_2$CH$_2$CH$_2$)$_2$CHNHCO-phenyl-4-OCF$_3$.

The alkylene radicals designated above as Y' and Y'' each has from one to four carbon atoms and are illustrated by —CH$_2$—,

—(CH$_2$)$_2$—, —(CH$_2$)$_3$—, —(CH$_2$)$_4$—, —CH(CH$_3$)(CH$_2$)$_2$— and

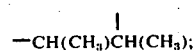

Y'' also can be a direct linkage. Thus, illustrations of Y'—Z—Y'' are

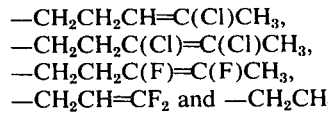

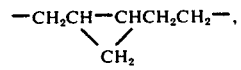

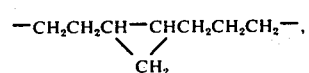

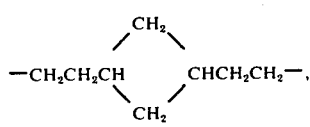

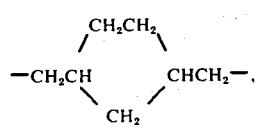

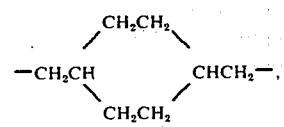

and the like.

The invention sought to be patented in a process aspect is described as residing in the process for the preparation of the symmetrical compounds of formula I (where $R_1$ is Q—O, R=R', $R_2=R_4$ and $R_3=R_4$), II or III which comprises reacting a diamine of formula IV $$\text{RNH—Y—NHR} \qquad \text{IV}$$

with a 4-(Q-O)-2(or 3)-$R_2$-5(or 6)-$R_3$-benzoylating, 3,4-methylenedioxybenzoylating or 4-(Q'-O)-2(or 3)-$R_2$-5(or 6)-$R_3$-benzoylating agent, preferably with at least two molar equivalents of a benzoyl halide of formula V

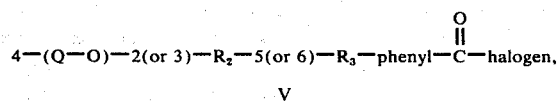

a 3,4-methylenedioxybenzoyl halide or a 4-(Q'-O)-2(or 3)-$R_2$-5(or 6)-$R_3$-benzoyl halide, respectively, where Y, R, R', Q, Q', $R_1$, $R_2$, $R_3$, $R_4$ and $R_5$ are defined as above in the definitions of formulas I, II and III. Other benzoylating agents are noted hereinbelow.

The invention sought to be patented in another process aspect is described as residing in the process for the preparation of the unsymmetrical compounds of formula I (where $R_1$ is other than Q—O—) which comprises reacting an N-aminoalkylbenzamide of the formula VI

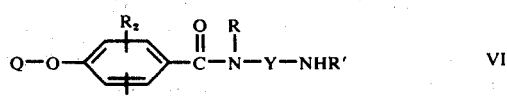

with a 4-$R_1$-2(or 3)-$R_4$-5(or 6)-$R_5$-benzoylating agent, where Q, R, R', Y, $R_1$, $R_2$, $R_3$, $R_4$ and $R_5$ have the meanings given above for formula I. Alternatively, these unsymmetrical compounds of formula I can be prepared by reacting an N-aminoalkylbenzamide of the formula VII

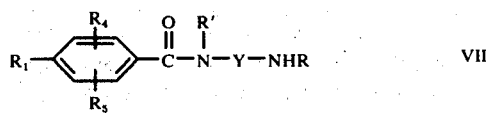

with a 4-(Q-O)-2(or 3)-$R_2$-5(or 6)-$R_3$-benzoylating agent.

Another process aspect of the invention resides in the process for the preparation of the N-aminoalkylbenzamide of formula VI where R and R' are each hydrogen which comprises reacting an aminoalkanonitrile of the formula $H_2N$—Y'—CN (VIII), where Y' has one $CH_2$ less than Y, with a 4-(Q—O)-2(or 3)-$R_2$—5(or 6)-$R_3$-benzoylating agent and reducing the resulting N-(CH-Y')-4-(Q-O)-2(or 3)-$R_2$-5(or 6)-$R_2$-benzamide where Q, Y, $R_2$ and $R_3$ have the meanings given for formula I. The N-aminoalkylbenzamide of formula VII is similarly prepared by first reacting an aminoalkanonitrile of formula VIII with a 4-$R_1$-2(or 3)-$R_4$-5(or 6)-$R_5$-benzoylating agent and reducing the corresponding N-(CH-Y')-4-$R_1$-2(or 3)-$R_4$-5(or 6)-$R_5$-benzamide.

The nature of the starting materials, mode of synthesis, results of elementary analyses, examination of the final products of formulas, I, II and III by infrared and nuclear magnetic resonance spectrographic analyses, all taken together, confirm the molecular structure assigned to these compounds.

The manner and process of making and using the invention will now be generally described so as to enable a person skilled in the art of medicinal chemistry to make and use the same, as follows:

The intermediate diamines, cyanoalkylamines and benzoyl halides are either commercially available or are readily prepared using known starting materials, e.g., from the corresponding benzoic acids, and using known methods, as illustrated hereinbelow in the specific examples.

The symmetrical final products, as illustrated by formulas I, II or III, are preferably prepared by reacting the appropriate diamine of formula IV with the benzoyl halide of formula V, a 3,4-methylenedioxybenzoyl halide or a 4-(Q'-O)-2(or 3)-$R_2$-5(or 6)-$R_3$-benzoyl halide, respectively, in the presence of an acid-acceptor, that is, a basic substance capable of neutralizing the hydrogen halide formed by the reaction, for example, an alkali carbonate, preferably sodium carbonate or potassium carbonate, an alkali hydroxide, preferably sodium hydroxide or potassium hydroxide. The reaction was carried out preferably by carefully mixing the reactants with cooling (to about 0° to 10° C.) and stirring in a medium comprising water and a suitable water-immiscible organic solvent inert under the reaction conditions, e.g., ethylene dichloride, chloroform, methylene dichloride, benzene, ether, and the like; the reaction mixture preferably was then allowed to warm up to room temperature and to stand with stirring until the reaction was completed. The unsymmetrical compounds of formula I are similarly prepared by first benzoylating a cyanoalkylamine of formula VI, reducing the N-cyanoalkylbenzamide and then benzoylating the resulting N-aminoalkylbenzamide. The reduction of the N-cyanoalkylbenzamides to the corresponding N-aminoalkylbenzamides can be carried out by using any reducing agent capable of reducing alkanonitriles to alkylamines, e.g., using an alkali aluminum hydride or by catalytic hydrogenation in the presence of a suitable catalyst, e.g., Raney nickel.

Alternatively, other available benxoylating agents can be used in place of said benzoyl halides in the process of the invention. For example, the reaction can be carried out by heating a lower-alkyl 4-(Q-O)-2(or 3)-$R_2$-5(or 6)-$R_3$-benzoate, lower-alkyl 3,4-methylenedioxybenzoate or lower-alkyl 4-(Q'-O)-2(or 3)-$R_2$-5(or 6)-$R_3$-benzoate with a diamine of formula IV or by reacting a 4-(Q-O) -2(or 3)-$R_2$-5(or 6)-$R_3$-benzoic, 3,4-methylenedioxybenzoic or 4-(Q'-O)-2(or 3)-$R_2$-5(or 6)-$R_3$-benzoic anhydride with said diamine to form the final products of formulas I, II or III, respectively. Also, the products of formula I, II or III are obtained by heating said diamine with a 4-(Q-O)-2(or 3)-$R_2$-5(or 6)-$R_3$-benzoic, 3,4-methylenedioxybenzoic or 4-(Q'-O)-2(or 3)-$R_2$-5(or 6)-$R_3$-benzoic acid either in the absence or presence of a suitable solvent, for example, dimethylformamide, tetrahydrofuran, benzene, ethylene dichloride, and the like, and either in the absence or presence of a dehydrating or an activating agent, e.g., dicyclohexycarbodiimide, 1,1-carbonyldiimidazole and the like.

The best mode comtemplated for carrying out the invention will now be set forth as follows:

1. N,N'-Pentamethylenebis(4-methoxybenzamide)

A solution containing 18.8 g. of 4-methoxybenzoyl chloride in 100 ml. of ethylene dichloride was added dropwise over a period of about 15 minutes with stirring to a cooled mixture containing 5.1 g. of 1,5-pentanediamine, 200 ml. 10% aqueous sodium hydroxide solution and 500 ml. of ethylene dichloride. The reaction mixture was stirred with cooling for an additional thirty minutes. The white precipitate was collected, washed with water, recrystallized from isopropyl alcohol and dried at about 60° C. in vacuo for about 15 hours to yield 14.4 g. of N,N'-pentamethylenebis(4-methoxybenzamide), m.p. 160°–161° C.

2. N,N'-Hexamethylenebis(4-methoxybenzamide)

m.p. 177°–178° C., 18.1 g., was prepared as in Example 1 using 18.8 g. of 4-methoxybenzoyl chloride in 100 ml. of ethylene dichloride, 5.8 g. of 1,6-hexanediamine, 200 ml. of 10% aqueous sodium hydroxide solution and 500 ml. of ethylene dichloride.

3. N,N'-Heptamethylenebis(4-methoxybenzamide)

m.p. 157°–159° C., 200 g., was prepared as in Example 1 using 213 g. of 4-methoxybenzoyl chloride in 350 ml. of ethylene dichloride, 82 g. of 1,7-heptanediamine, 105 ml. of 35% aqueous sodium hydroxide plus 135 ml. of water, 500 ml. of ethylene dichloride and 300 ml. of water. Instead of recrystallizing the product it was purified as follows: it was first slurried with three liters of methanol for about a hour, collected, washed with three 100 ml. portions of cold methanol and reslurried in three liters of n-hexane, washed with three 100 ml. portions of n-hexane and dried at 60° C. in vacuo for 20 hours.

The above product also is prepared by heating, preferably in a suitable solvent, e.g., ethylene dichloride or benzene, 1,7-heptanediamine and either 4-methoxybenzoic anhydride, ethyl 4-methoxybenzoate or 4-methoxybenzoic acid, the latter optionally being used in conjunction with dicyclohexylcarbodiimide.

4. N,N'-Octamethylenebis(4-methoxybenzamide)

m.p. 175°–176° C., 16.3 g., was prepared as in Example 1 using 18.8 g. of 4-methoxybenzoyl chloride in 100 ml. of ethylene dichloride, 7.2 g. of 1,8-octanediamine, 200 ml. of 10% aqueous sodium hydroxide solution, 500 ml. of ethylene dichloride and recrystallization from ethanol.

5. N,N'-Nonamethylenebis(4-methoxybenzamide)

m.p. 156°–157° C., 15.8 g., was prepared as in Example 1 using 18.8 g. of 4-methoxybenzoyl chloride in 100 ml. of ethylene dichloride, 7.9 g. of 1,9-nonanediamine, 200 ml. of 10% aqueous sodium hydroxide solution and 500 ml. of ethylene dichloride.

6. N,N'-Heptamethylenebis(4-ethoxybenzamide)

m.p. 156°–157° C., 20.7 g., was prepared as in Example 1 using a solution of 4-ethoxybenzoyl chloride (this acid halide was prepared from 41.5 g. of 4-ethoxybenzoic acid as described below) in 200 ml. of ethylene dichloride, 13.0 g. of 1,7-heptanediamine, 250 ml. of 10% aqueous potassium hydroxide solution, 500 ml. of ethylene dichloride and recrystallization from ethanol using decolorizing charcoal.

The above intermediate 4-ethoxybenzoyl chloride was prepared as follows: A mixture containing 41.5 g. of 4-ethoxybenzoic acid and excess thionyl chloride was heated on a steam bath for about 15 minutes until the evolution of hydrogen chloride ceased; 100 ml. of ethylene dichloride was added and removed by distillation; another 200 ml. of ethylene dichloride was added; the mixture was filtered and the filtrate evaporated in vacuo on a steam bath to remove the ethylene dichloride; the remaining oily 4-ethoxybenzoyl chloride which solidified on cooling, was dissolved in 200 ml. of ethylene dichloride and used in the above said reaction.

7. N,N'-Heptamethylenebis(4-isopropoxybenzamide)

m.p. 135°–136° C., 10.9 g., was prepared as in Example 1 using a solution of 4-isopropoxybenzoyl chloride (from 18.0 g. of 4-isopropoxybenzoic acid as in Example 6) in 100 ml. of ethylene dichloride, 8.9 g. of 1,7-heptanediamine, 200 ml. of 10% aqueous potassium hydroxide solution, 500 ml. ethylene dichloride and recrystallization from acetonitrile using decolorizing charcoal.

8. N,N'-Heptamethylenebis(4-n-butoxybenzamide)

m.p. 151°–152° C., 20.0 g., was prepared as in Example 1 using 4-n-butoxybenzoyl chloride (prepared from 27.2 g. of 4-n-butoxybenzoic acid as in Example 6) in 200 ml. of ethylene dichloride, 6.5 g. of 1,7-heptanediamine, 200 ml. of 10% aqueous potassium hydroxide solution, 500 ml. of ethylene dichloride and recrystallization from ethanol using decolorizing charcoal.

9. N,N'-Heptamethylenebis(4-pentyloxybenzamide)

m.p. 155°–156° C., 29.9 g., was prepared as in Example 1 using 50 g. of 4-pentyloxybenzoyl chloride in 200 ml. of ethylene dichloride, 13.0 g. of 1,7-heptanediamine, 250 ml. of 10% aqueous potassium hydroxide solution, 500 ml. of ethylene dichloride and recrystallization from ethanol.

10. N,N'-Hexamethylenebis(3,4-methylenedioxybenzamide)

m.p. 183°–185° C., 19.4 g., was prepared as in Example 1 using 3,4-methylenedioxybenzoyl chloride (from 30 g. of 3,4-methylenedioxybenzoic acid as in Example 6) in 100 ml. of ethylene dichloride, 9.3 g. of 1,6-hexanediamine, 200 ml. of 10% aqueous potassium hydroxide solution, 500 ml. of ethylene dichloride and recrystallization from ethanol using decolorizing charcoal.

11.
N,N'-Heptamethylenebis(3,4-methylenedioxybenzamide)

m.p. 151°–152° C., 24.9 g., was prepared as in Example 1 using 3,4-methylenedioxybenzoyl chloride (prepared as in Example 6 using 30 g. of 3,4-methylenedioxybenzoic acid) in 150 ml. of ethylene dichloride, 10.5 g. of 1,7-heptanediamine, 200 ml. of 10% aqueous potassium hydroxide solution, 500 ml. of ethylene dichloride and recrystallization from ethanol using decolorizing charcoal.

12.
N,N'-Octamethylenebis(3,4-methylenedioxybenzamide)

m.p. 179°–180° C., 21.6 g., was prepared as in Example 1 using 3,4-methylenedioxybenzoyl chloride (from 30 g. of 3,4-methylenedioxybenzoic acid as in Example 6) in 100 ml. of ethylene dichloride, 11.5 g. of 1,8-octanediamine, 200 ml. of 10% aqueous potassium hydroxide solution, 500 ml. of ethylene dichloride and recrystallization from ethanol.

13.
N,N'-Heptamethylenebis(3,4-dimethoxybenzamide)

m.p. 160°–161° C., 13.2 g., was prepared as in Example 1 using 3,4-dimethoxybenzoyl chloride (from 25.5 g. of 3,4-dimethoxybenzoic acid as in Example 6) in 150 ml. of ethylene dichloride, 6.5 g. of 1,7-heptanediamine, 200 ml. of 10% aqueous potassium hydroxide solution, 500 ml. of ethylene dichloride and recrystallizations from ethanol and methanol using decolorizing charcoal.

14.
N,N'-Heptamethylenebis(3-chloro-4-methoxybenzamide)

m.p. 132°–133° C., 16.4 g., was prepared as in Example 1 using 3-chloro-4-methoxybenzoyl chloride (from 25.0 g. of 3-chloro-4-methoxybenzoic acid as in Example 6) in 200 ml. of ethylene dichloride, 7.8 g. of 1,7-heptanediamine, 200 ml. of 10% aqueous potassium hydroxide solution, 500 ml. of ethylene dichloride and recrystallization from acetonitrile using decolorizing charcoal.

15.
N,N'-Hexamethylenebis(4-trifluoromethoxybenzamide)

A solution containing 9 g. of 4-trifluoromethoxybenzoyl chloride in 150 ml. of ethylene dichloride was added slowly with stirring and cooling to a mixture containing 2.03 g. of 1,6-hexanediamine, 100 ml. of 10% aqueous potassium hydroxide solution and 300 ml. of ethylene dichloride. The mixture was then stirred without cooling while allowing the temperature to come up to room temperature (about 25°–30° C.). The separated white solid was collected, recrystallized from methanol using decolorizing charcoal and dried in a vacuum oven at about 60° C. to yield 4.9 g. of N,N'-hexamethylenebis(4-trifluoromethoxybenzamide), m.p. 179°–180° C.

16.
N,N'-Heptamethylenebis(4-trifluoromethoxybenzamide)

A mixture containing 28.8 g. of 4-trifluoromethoxybenzoic acid and an excess of thionyl chloride was heated on a steam bath under reflux for three hours. The excess thionyl chloride was distilled off by heating on the steam bath. Fifty ml. of ethylene dichloride was added and removed by heating in vacuo, more ethylene dichloride was added and removed by distilling in vacuo. The remaining residue, 4-trifluoromethoxybenzoyl chloride, was dissolved in 100 ml. of ethylene dichloride and added slowly with stirring and cooling to a mixture containing 8.45 g. of 1,7-heptanediamine, 250 ml. of 10% aqueous potassium hydroxide solution and 500 ml. of ethylene dichloride. The mixture was stirred with cooling for another 5 minutes and then allowed to stand overnight (about 15 hours). The white solid was collected, washed with water, recrystallized from methanol and dried in vacuo at 60° C. to yield 21.4 g. of N,N'-heptamethylenebis(4-trifluoromethoxybenzamide), m.p. 150°–151° C.

17.
N,N'-Octamethylenebis(4-trifluoromethoxybenzamide)

m.p. 164°–165° C., 12.0 g., was prepared as in Example 16 using 4-trifluoromethoxybenzoyl chloride (from 16.5 g. of 4-trifluoromethoxybenzoic acid as in Example 16) in 150 ml. of ethylene dichloride, 7.2 g. of 1,8-octanediamine, 200 ml. of 10% aqueous potassium hydroxide solution, 500 ml. of ethylene dichloride and recrystallization from methanol using decolorizing charcoal.

18.
N,N'-Heptamethylenebis(4-trichloromethoxybenzamide)

A solution containing 12.1 g. of 4-trichloromethoxybenzoyl chloride in 40 ml. of ethylene dichloride was added slowly with stirring to a mixture containing 2.7 g. of 1,7-heptanediamine, 60 ml. of 10% aqueous potassium hydroxide solution and 90 ml. of ethylene dichloride, said mixture cooled in an ice bath. Stirring and cooling of the mixture were continued for about 20 minutes after addition of the acid chloride. In order to facilitate filtration of the separated solid, sodium chloride was first added with little success and then a large amount of n-pentane was added with stirring. The solid was then collected, dried overnight in a vacuum oven at 60° C. The solid was purified by first dissolving it in 300 ml. of chloroform, filtering the cloudy solution through infusorial earth, evaporating the chloroform solution to dryness, recrystallizing the remaining solid successively from acetonitrile and benzene, and drying in vacuo to yield 5.9 g. of N,N'-heptamethylenebis(4-trichloromethoxybenzamide), m.p. 152°–153° C. with decomposition.

19.
N,N'-Heptamethylenebis[4-(2-chloro-1,1,2-trifluoroethoxy)benzamide]

m.p. 153°–154° C., 16.0 g., was prepared as in Example 16 using 4-(2-chloro-1,1,2-trifluoroethoxy)benzoyl chloride (from 23.0 g. of the corresponding acid as in Example 16) in 150 ml. of ethylene dichloride, 5.8 g. of 1,7-heptanediamine, 200 ml. of 10% aqueous potassium hydroxide solution, 500 ml. of ethylene dichloride and recrystallization from acetonitrile using decolorizing charcoal.

20. N,N'-(1,7-Dimethylheptamethylene)bis(4-trifluoromethoxybenzamide)

A solution containing 12.8 g. of 4-trifluoromethoxybenzoyl chloride in 50 ml. of ethylene dichloride was added dropwise with stirring to a mixture of 4.50 g. of 2,8-nonanediamine, 8.42 g. of potassium carbonate and 100 ml. of ethylene dichloride, the latter mixture being at 10° C. The reaction mixture was stirred while allowing its temperature to rise to room temperature (about 25°–30° C.) and was then stored at 5° C. overnight (about sixteen hours). The precipitated white solid was collected, washed well with water and dried to yield 12.2 g. of white needles. The filtrate was separated and the aqueous portion was extracted with one 100 ml. portion of ethylene dichloride. The extract was combined with the ethylene dichloride portion of the filtrate and the combined solution was dried successively over anhydrous sodium sulfate and anhydrous potassium carbonate. Removal of the solvent under reduced pressure left 2.6 g. of a pale yellow oil which completely crystallized on standing at room temperature. The 12.2 and 2.6 g. portions of crystalline product were combined and recrystallized from 95% ethanol-benzene and dried in vacuo at 50° C. for eighteen hours to yield 11.5 g of N,N'-(1,7-dimethylheptamethylene)-bis(4-trifluoromethoxybenzamide), m.p. 156°–160° C.

The intermediate 2,8-nonanediamine was prepared by reducing the dioxime of 2,8-nonanedione as follows: A solution containing 32.2 g. of the dioxime of 2,8-nonanedione in 150 ml. of 95% ethanol was hydrogenated in the presence of Raney nickel catalyst, the initial pressure and temperature being 1600 p.s.i. and 50° C. and the final pressure and temperature being 340 p.s.i. and 18° C. The reduction was completed in about 2½ hours. The catalyst was filtered off and the filtrate distilled in vacuo to remove the solvent. The remaining oil was distilled under reduced pressure to yield an 18.1 g. fraction distilling at 75°–83° C. at 0.3–0.5 mm. A second vacuum distillation yielded 16.2 g. of 2,8-nonanediamine, b.p. 64°–68° C. at 0.50–0.90 mm.

21. N,N'-[Methyliminobis(trimethylene)]bis(4-trifluoromethoxybenzamide)

To a stirred mixture containing 2.5 g. of methyliminobis(n-propylamine), 20 ml. of ethylene dichloride, 4.75 g. of anhydrous potassium carbonate and 45 ml. of water cooled to about 5°–10° C. was added dropwise a solution containing 7.7 g. of 4-trifluoromethoxybenzoyl chloride in 20 ml. of ethylene dichloride. The reaction mixture was allowed to stand overnight in a refrigerator and then shaken well with chloroform. The chloroform extract was dried under anhydrous potassium carbonate, concentrated in vacuo to remove the chloroform and residue recrystallized from ethylene dichloride-n-hexane to yield 5.4 g. of N,N'-[methyliminobis(trimethylene)]bis(4-trifluoromethoxybenzamide), m.p. 110°–111° C.

22. N,N'-[Methyliminobis(trimethylene)]bis(N-methyl-4-trifluoromethoxybenzamide)

5.6 g. as a dark orange oil, was prepared as in Example 21 using 4.9 g. of N,N'-dimethylmethyliminobis(di-n-propylamine), 50 ml. of ethylene dichloride, 7.84 g. of potassium carbonate, 70 ml. of water, 13.2 g. of 4-trifluoromethoxybenzoyl chloride and 40 ml. of ethylene dichloride. The product was obtained by vacuum distillation of the chloroform from the dried chloroform extract.

23. N,N'-Oxybis(trimethylene)bis(4-trifluoromethoxybenzamide)

A solution containing 3.96 g. of bis(3-aminopropyl) ether in 150 ml. of ethylene dichloride was combined with a solution containing 8.42 g. of anhydrous potassium carbonate in 100 ml. of water and the resulting mixture was chilled in an ice bath with stirring. To this chilled mixture at about 5° C. was added dropwise with stirring over a period of 90 minutes a solution containing 13.5 g. of 4-trifluoromethoxybenzoyl chloride in 50 ml. of ethylene dichloride. The mixture was stirred for an additional 2 hours while allowing the reaction mixture to warm up to room temperature; it was then stored at 5° C. for 48 hours. The precipitated solid was collected, washed well with water and dried to yield 12.1 g. of finely crystalline material. The organic layer was separated from the filtrate and the aqueous layer extracted with ethylene dichloride. The extract was combined with the organic layer from the filtrate and the combined solution was extracted with brine, dried over anhydrous calcium sulfate and the solvent removed by vacuum distillation to yield 3.27 g. of colorless oil which crystallized at room temperature. The combined 12.1 and 3.27 g. of crystalline product was recrystallized from benzene and dried at 50° C. at 18 hours at one-third atmosphere to yield 12.76 g. of N,N'-oxybis(trimethylene)bis(4-trifluoromethoxybenzamide), m.p. 118.5°–119.5° C. (corr.).

24. Ethylene ketal of N,N'-(4-oxoheptamethylene)bis(4-trifluoromethoxybenzamide)

m.p. 136.5°–137.5° C., 12.2 g., was prepared as in Example 20 using 36.3 g. of 4-trifluoromethoxybenzoyl chloride in 50 ml. of ethylene dichloride, 15.2 g. of the ethylene ketal of 1,7-diamino-4-heptanone, 23.4 g. of potassium carbonate, 300 ml. of ethylene dichloride, 150 ml. of water and recrystallization from benzene-n-hexane.

The intermediate ethylene ketal of 1,7-diamino-4-heptanone was prepared in two steps as follows: A suspension of 97.0 g. of potassium phthalimide in 300 ml. dimethylformamide was stirred and heated on a steam bath. To this hot solution was added with stirring 59.8 g. of the ethylene ketal of 1,7-dichloro-4-heptanone in 300 ml. of dimethylformamide and the resulting mixture was heated with stirring for 5 hours. The hot reaction mixture was filtered and the filtrate evaporated in vacuo to remove the solvent. The residual solid was dissolved in chloroform and chloroform solution filtered. The solid obtained by filtering the hot reaction mixture was digested with 150 ml. of chloroform and the mixture filtered. The two chloroform filtrates were combined, washed with three 200 ml. portions of water, and then with brine, dried over anhydrous magnesium sulfate and distilled in vacuo to remove the solvent. The remaining white crystalline solid was recrystallized from methanolchloroform to yield 79.6 g. of the ethylene ketal of N,N'-(4-oxoheptamethylene)bis(phthalimide), m.p. 147°–148° C. A solution containing 48.8 g. of N,N'-(4-oxoheptamethylene)bis(phthalimide) in 300 ml. of 95% ethanol was stirred and heated on a steam bath and 12 g. of 85% hydrazine hydrate was added. In a few minutes the mixture became clear and the resulting solution was boiled under reflux for 2 hours. During the reaction a voluminous white precipitate separated. About 200 ml. of water was added to dissolve the precipitate and most of the alcohol was removed by distillation under reduced pressure. The resulting solution was allowed to stand overnight (about 16 hours). The resulting white crystalline mass was warmed to room temperature, water was added and the resulting mixture was extracted with four 100 ml. portions of methylene dichloride. The combined extracts were dried over anhydrous potassium carbonate and the solvent removed by distillation under reduced pressure to leave 15.5 g. of clear viscous liquid. The above aqueous portion was extracted with methylene dichloride, the extract dried over anhydrous potassium carbonate and heated in vacuo to remove the solvent, thereby yielding an additional 5.2 g. portion of clear viscous liquid. The 15.5 and 5.2 g. portions of liquid were combined and distilled under pressure to yield 14.6 g. of the ethylene ketal of 1,7-diamino-4-heptanone, b.p. 104° C. at 0.2 mm.

25. N,N'-(4-Oxoheptamethylene)bis(4-trifluoromethoxybenzamide)

A 23.5 g. portion of the ethylene ketal of N,N'-(4-oxoheptamethylene)bis(4-trifluoromethoxybenzamide) was dissolved in 200 ml. of 95% ethanol; 50 ml. of water and 50 ml. 6N hydrochloric acid were added; and the resulting mixture was refluxed for 2 hours. About 100 ml. of ethanol was then distilled off and the remaining solution was filtered and allowed to cool to room temperature. The resulting precipitate was collected, washed successively with water and water-ethanol and dried at 70° C. and one-third atmosphere for 4 hours to yield 18.0 g. of N,N'-(4-oxoheptamethylene)bis(4-trifluoromethoxybenzamide), m.p. 151°–152° C.

26. N,N'-(trans-1,4-cyclohexylenedimethylene)bis(4-trifluoromethoxybenzamide)

m.p. 279°–280° C., 8.8 g., was prepared as in Example 23 using 3.44 g. of trans-1,4-cyclohexanebis(methylamine) in 25 ml. of ethylene dichloride, 6.74 g. of potassium carbonate, 66 ml. of water, 10.85 g. of 4-trifluoromethoxybenzoyl chloride in 25 ml. of ethylene dichloride and successive recrystallizations from methanolbenzene and acetonitrile.

27. N,N'-Heptamethylenebis(4-cyclohexyloxybenzamide)

m.p. 144°–145° C., 27.3 g., was prepared as in Example 1 using 4-cyclohexyloxybenzoyl chloride (from 42.0 g. of the corresponding acid as in Example 6) in 100 ml. of ethylene dichloride, 11.7 g. of 1,7-heptanediamine, 200 ml. of 10% potassium hydroxide solution, 500 ml. of ethylene dichloride and recrystallization from acetonitrile using decolorizing charcoal.

28. N,N'-Heptamethylenebis(4-phenoxybenzamide)

m.p. 164°–165° C., 9.9 g., was prepared as in Example 23 using 12.0 g. of 4-phenoxybenzoyl chloride (from 16.0 g. of 4-phenoxybenzoic acid as in Example 6) in 20 ml. of ethylene dichloride, 3.8 g. of 1,7-heptanediamine, 40 ml. of ethylene dichloride, 6.9 g. of potassium carbonate, 63 ml. of water and recrystallization from ethylene dichloride.

29. N,N'-Heptamethylenebis[4-(2-diethylaminoethoxy)-benzamide]

A mixture containing 14.8 g. of N,N'-heptamethylenebis(4-hydroxybenzamide), 16.3 g. of 2-diethylaminoethyl chloride, 20.7 g. of potassium carbonate and 500 ml. of isoamyl alcohol was heated at reflux for 8 hours and then allowed to stand overnight (about 16 hours). To the reaction mixture was added 150 ml. of water which dissolved the white precipitate. The entire reaction mixture was then evaporated to dryness in vacuo on a steam bath. To the remaining solid was added water; the mixture was stirred for 3 hours and then filtered. The solid was then recrystallized twice from acetonitrile using decolorizing charcoal each time and dried in a vacuum desiccator to yield 15.6 g. of N,N'-heptamethylenebis[4-(2-diethylaminoethoxy)-benzamide], m.p. 130°–131° C.

The intermediate N,N'-heptamethylenebis(4-hydroxybenzamide) was prepared in several steps as follows: A mixture containing 354 g. of 4-hydroxybenzoic acid and 1000 g. of acetyl chloride was heated on a steam bath at reflux whereupon there separated 4-acetoxybenzoic acid. To the mixture was added 500 g. of thionyl chloride and the resulting reaction mixture was heated at reflux until the solid dissolved and the solution was then allowed to stand overnight. The excess thionyl chloride was then removed by distillation. Ethylene dichloride was next added and removed by distilling in vacuo on a steam bath to yield, as an orange oil, 4-acetoxybenzoyl chloride. A solution containing 317 g. of 4-acetoxybenzoyl chloride in 500 ml. of ethylene dichloride was added slowly over a period of about 1 hour with stirring to a cooled mixture containing 100 g. of 1,7-heptanediamine, 100 ml. of 10% aqueous potassium hydroxide solution and 1500 ml. of ethylene dichloride. The resulting precipitate was collected, dried and dissolved by heating with 10% aqueous potassium hydroxide solution. The alkaline solution was acidified with 6N hydrochloric acid and the resulting gummy precipitate was collected and dissolved in ethanol. The ethanol solution was dried over anhydrous magnesium sulfate and the solvent removed by distilling in vacuo. The remaining yellow oil, which turned to a glassy material on cooling, was treated with acetic anhydride and the resulting mixture heated on a steam bath with stirring for 4 hours. The hot solution was then allowed to cool to room temperature. The resulting precipitate was collected and recrystallized twice from acetonitrile, using decolorizing charcoal during the first recrystallization, and dried in a vacuum oven to yield 72.7 g. of N,N'-heptamethylenebis(4-acetoxybenzamide), m.p. 180°–181° C. A 49.5 g. portion of the N,N'-heptamethylenebis(4-acetoxybenzamide) was mixed with 400 ml. of 10% aqueous potassium hydroxide solution and the mixture heated for about 16 hours with stirring. The resulting solution was then allowed to cool and acidified with 3N hydrochloric acid. The resulting precipitate was collected and dried in a vacuum oven to yield 34.6 g. of N,N'-heptamethylenebis(4-hydroxybenzamide), m.p. 179°–181° C.

30.
N,N'-Heptamethylenebis(4-cyclopentyloxybenzamide)

m.p. 153°–154° C., 18.8 g., was prepared as in Example 29 using 18.5 g. of N,N'-heptamethylenebis(4-hydroxybenzamide), 29.8 g. of cyclopentyl bromide, 20.7 g. of potassium carbonate, 500 ml. of isoamyl alcohol and recrystallization from acetonitrile.

31.
N,N'-(cis-1,4-Cyclohexylenedimethylene)bis(4-methoxybenzamide)

m.p. 224°–226° C., 13.2 g., was prepared as in Example 1 using 18.8 g. of 4-methoxybenzoyl chloride, 7.1 g. of cis-1,4-bis(aminomethyl)cyclohexane, 200 ml. of 10% aqueous sodium hydroxide solution, 600 ml. of ethylene dichloride and recrystallization from acetic acid.

32.
N,N'-(trans-1,4-Cyclohexylenedimethylene)bis(4-methoxybenzamide)

m.p. 258°–260° C., 16.5 g., was prepared as in Example 1 using 18.8 g. of 4-methoxybenzoyl chloride, 7.1 g. of trans-1,4-bis(aminomethyl)cyclohexane, 200 ml. of 10% aqueous potassium hydroxide solution, 600 ml. of ethylene dichloride and recrystallization from acetic acid.

33.
N,N'-(1,4-Phenylenedimethylene)bis(4-methoxybenzamide)

m.p. 249°–250° C., 10.0 g., was prepared as in Example 1 using 18.8 g. of 4-methoxybenzoyl chloride, 6.6 g. of 1,4-bis(aminomethyl)benzene, 200 ml. of 10% aqueous sodium hydroxide solution, 600 ml. of ethylene dichloride and recrystallization from acetic acid.

34.
N,N'-Heptamethylenebis(4-trideuteromethoxybenzamide)

To a stirred mixture containing 6.9 g. of 1,7-heptanediamine, 69 ml. of 10% aqueous potassium hydroxide solution and 75 ml. of ethylene dichloride chilled in an ice bath was added dropwise over a period of 35 minutes a solution containing 18.5 g. of 4-trideuteromethoxybenzoyl chloride in 50 ml. of ethylene dichloride. The ice bath was removed and the reaction mixture containing a white solid precipitate was stirred for an additional 15 minutes. The solid was then collected by filtering through a sintered glass funnel, recrystallized from acetonitrile and air-dried to yield 14.8 g. of N,N'-heptamethylenebis(4-trideuteromethoxybenzamide), m.p. 156°–159° C. This compound chemically is the same as N,N'-heptamethylenebis(4-methoxybenzamide) of Example 3 except that it has heavy hydrogen atoms of mass 2, i.e., deuterium, in place of the six hydrogen atoms of the two 4-methoxy groups of said compound of Example 3 and biologically has the same applied use characteristics disclosed hereinabove; in fact, the compound of Example 34 has been found to have even a greater antifertility activity in female rats than the compound of Example 3.

The intermediate 4-trideuteromethoxybenzoyl chloride was prepared in several steps as follows: To a stirred mixture containing 4.9 g. of ethyl 4-hydroxybenzoate and 6.2 g. of anhydrous potassium carbonate in 65 ml. of acetone was added 5.0 g. of trideuteromethyl iodide and the resulting mixture was refluxed on a steam bath with stirring for 4½ hours. The solid inorganic material was filtered off and rinsed with acetone. The combined filtrates were evaporated and the residual material was taken up in a mixture of water and chloroform. The resulting mixture was made strongly basic by 10% aqueous potassium hydroxide solution, shaken well and the chloroform layer separated. The aqueous layer was extracted again with fresh chloroform. The combined chloroform extracts were dried over solid potassium carbonate, the mixture filtered and the filtrate evaporated in vacuo to yield a yellow oil which was distilled under reduced pressure to yield 4.4 g. of ethyl 4-trideuteromethoxybenzoate, b.p. 137°–140° C. at 15 mm. The NMR spectral analysis of said ester confirmed that the methoxy groups were still fully deuterated. Another run starting with 19.6 g. of ethyl 4-hydroxybenzoate, 15.0 g. of trideuteromethyl iodide, 24.8 g. of potassium carbonate and 260 ml. of acetone yielded 18.1 g. of ethyl 4-trideuteromethoxybenzoate.

A mixture containing 20.9 g. of ethyl 4-trideuteromethoxybenzoate and 125 ml. of 10% aqueous potassium hydroxide solution was refluxed on a steam bath for 90 minutes, cooled and diluted with 375 ml. of water. The solution was filtered through a sintered glass funnel to remove some slight turbidity and the filtrate was acidified with stirring using 12N hydrochloric acid whereupon a white solid separated. After the mixture had been stirred for 15 minutes, the solid was collected, rinsed with a small quantity of water and dried in a vacuum oven at 60° C. to yield 16.6 g. of 4-trideuteromethoxybenzoic acid, m.p. 185°–186° C.

A mixture containing 16.6 g. of 4-trideuteromethoxybenzoic acid and 166 ml. of thionyl chloride was stirred and heated on a steam bath for 90 minutes. Excess thionyl chloride was distilled off first at atmospheric pressure and then in vacuo. About 100 ml. of ethylene dichloride was added to the residue and the mixture evaporated in vacuo to remove last traces of thionyl chloride. There was obtained a quantitative yield of 4-trideuteromethoxybenzoyl chloride as a pale yellow liquid.

35.
N,N'-Heptamethylenebis[4-(2,2,2-trifluoroethoxy)benzamide]

m.p. 167°–168° C., 6.7 g., was prepared as in Example 1 using 8.7 g. of 4-(2,2,2-trifluoroethoxy)benzoyl chloride in 18 ml. of ethylene dichloride, 2.4 g. of 1,7-heptanediamine, 24 ml. of 10% aqueous potassium hydroxide solution, 27 ml. of ethylene dichloride and recrystallization from acetonitrile.

The above intermediate 4-(2,2,2-trifluoroethoxy)-benzoyl chloride was prepared in three steps as follows: A mixture containing 8.3 g. of ethyl 4-hydroxybenzoate, 10.4 g. of anhydrous potassium carbonate, 12.6 g. of 2,2,2-trifluoroethyl iodide and 100 ml. of dimethylformamide was refluxed with stirring on a steam bath for 24 hours. The reaction mixture was filtered and the filtrate was evaporated in vacuo to remove the solvent. The solid-liquid residue was poured into water and a small quantity of 10% aqueous potassium hydroxide solution was added to make the mixture strongly basic. The mixture was then extracted with chloroform. The chloroform extracts were washed with water, dried over anhydrous potassium carbonate and evaporated in vacuo to remove the chloroform. The remaining oil crystallized on cooling to yield 10.8 g. of ethyl 4-(2,2,2-trifluoroethoxy)benzoate.

A mixture containing 10.8 g. of ethyl 4-(2,2,2-trifluoroethoxy)benzoate and 65 ml. of 10% aqueous potassium hydroxide solution was stirred while heating on a steam bath under a reflux condenser for 4 hours. The hot reaction solution was filtered through a fine sintered glass funnel to remove some turbidity. The filtrate was diluted with an equal volume of water and the resulting pale yellow solution was stirred and acidified with 6N of hydrochloric acid. The copious white precipitate was collected, washed with water and dried in a vacuum oven at 60° C. to yield 8.3 g. of 4-(2,2,2-trifluoroethoxy)benzoic acid, m.p. 199°–201° C.

A mixture of 8.2 g. of 4-(2,2,2-trifluoroethoxy)benzoic acid and 82 ml. of thionyl chloride was stirred and refluxed on a steam bath for 1 hour. The excess thionyl chloride was distilled off at atmospheric pressure and then at reduced pressure. About 50 ml. of ethylene dichloride was added and the solution evaporated in vacuo to yield 8.7 g. of 4-(2,2,2-trifluoroethoxy)benzoyl chloride.

36.
N,N'-Heptamethylenebis[4-(2,2-dichlorovinyloxy)-benzamide]

m.p. 144°–145° C., 27.8 g., was prepared as in Example 1 using 31.7 g. of 4-(2,2-dichlorovinyloxy)benzoyl chloride in 85 ml. of ethylene dichloride, 7.8 g. of 1,7-heptanediamine, 85 ml. of 10% aqueous potassium hydroxide solution, 275 ml. of ethylene dichloride and recrystallization from absolute ethanol.

The above intermediate 4-(2,2-dichlorovinyloxy)-benzoyl chloride was prepared in three steps as follows: A mixture containing 49.8 g. of ethyl 4-hydroxybenzoate, 600 ml. of dimethylformamide, 62.0 g. of potassium carbonate, 2.0 g. of potassium iodide and 1,1,1,2-tetrachloroethane was heated on a steam bath with stirring for 72 hours. The inorganic solids were filtered off and washed with fresh dimethylformamide. The combined filtrate and washings were evaporated in vacuo and the remaining liquid residue was taken up with water and chloroform, aqueous potassium hydroxide solution was added to make the water layer strongly basic, the mixture was shaken well and the layers were separated. The aqueous layer was extracted with chloroform. The combined chloroform extracts were washed with water, stirred with anhydrous potassium carbonate and decolorizing charcoal, filtered and evaporated in vacuo to yield a pale yellow liquid. The liquid was distilled under reduced pressure to yield 55.2 g. of ethyl 4-(2,2-dichlorovinyloxy)benzoate, b.p. 174°–176° C. at 19 mm. A 22.7 g. portion of the ethyl 4-(2,2-dichlorovinyloxy)benzoate was redistilled at 15 mm. pressure through a 20 cm. vacuum jacketed Vigreux column insulated with glass wool and aluminum foil, thereby yielding a 19.7 g. fraction distilling at 180°–182° C. (15 mm.).

A mixture containing 31.3 g. of ethyl 4-(2,2-dichlorovinyloxy)benzoate and 180 ml. of 10% aqueous potassium hydroxide solution was stirred and heated on a steam bath for 2½ hours. The reaction mixture was then cooled in an ice bath, diluted with 180 ml. of water and the faintly turbid solution was filtered through a fine sintered glass funnel. The filtrate was stirred and acidified with 12N hydrochloric acid. Stirring was continued for 15 minutes and the white solid precipitate was collected, washed with water and dried in a vacuum oven at 60° C. to yield 27.8 g. of 4-(2,2-dichlorovinyloxy)benzoic acid, m.p. 131.5°–133° C.

A mixture containing 27.8 g. of 4-(2,2-dichlorovinyloxy)benzoic acid and 278 ml. of thionyl chloride was stirred and refluxed on a steam bath for 3 hours. The excess thionyl chloride was distilled off, first at atmospheric pressure and then at reduced pressure. Ethylene dichloride was added to the liquid residue and the solution evaporated in vacuo to remove the ethylene dichloride and remaining traces of thionyl chloride. There was thus obtained a quantitative yield of 4-(2,2-dichlorovinyloxy)benzoyl chloride as a pale yellow, non-volatile liquid.

37.
N,N'-Heptamethylenebis(4-allyloxybenzamide), m.p. 152°–153° C., 21.4 g., was prepared as in Example 1 using 28.5 g. of 4-allyloxybenzoyl chloride in 65 ml. of ethylene dichloride, 9.4 g. of 1,7-heptanediamine, 120 ml. of ethylene dichloride, 94 ml. of 10% aqueous potassium hydroxide solution and recrystallization from absolute ethanol.

The above intermediate 4-allyloxybenzoyl chloride was prepared in three steps as follows: A mixture containing 29.0 g. of allyl bromide, 33.2 g. of ethyl 4-hydroxybenzoate, 41.4 g. of potassium carbonate and 400 ml. of dimethylformamide was stirred and heated on a steam bath for 18 hours. The reaction mixture was filtered and the filtrate evaporated in vacuo. The remaining residue was taken up in chloroform and water followed by addition of a few ml. of 10% aqueous potassium hydroxide solution to make the aqueous layer strongly basic. The mixture was shaken well and the layers separated. The aqueous layer was extracted with chloroform. The combined chloroform filtrate and extract were washed with water, stirred with anhydrous potassium carbonate and decolorizing charcoal, and evaporated in vacuo to yield a yellow liquid residue which was dissolved in ether. The ether solution was extracted with two 100 ml. portions of 5% aqueous potassium hydroxide, stirred with anhydrous potassium carbonate and decolorizing charcoal, and evaporated in vacuo to yield 39.7 g. of ethyl 4-allyloxybenzoate.

A mixture containing 30 g. of ethyl 4-allyloxybenzoate and 180 ml. of 10% aqueous potassium hydroxide solution was stirred and heated on a steam bath for 2½ hours. The resulting reaction mixture was diluted with one volume of water and filtered through a sintered glass funnel. The filtrate was stirred and acidified with excess concentrated hydrochloric acid. More water was added in order to facilitate stirring. The copious white solid precipitate was collected and dried in a vacuum oven at 60° C. to produce a quantitative yield of 4-allyloxybenzoic acid, m.p. 163°–164° C.

A mixture containing 29.9 g. of 4-allyloxybenzoic acid and 250 ml. of thionyl chloride was stirred and refluxed for 90 minutes and the excess thionyl distilled off, first at atmospheric pressure and then at reduced pressure. Ethylene dichloride was added and the solution evaporated in vacuo to remove the ethylene dichloride and remaining traces of thionyl chloride to give a quantitative yield of 4-allyloxybenzoyl chloride.

38.
N,N'-(2,2,4-Trimethylhexamethylene)bis(4-trifluoromethoxybenzamide)

A solution containing 33.6 g. of 4-trifluoromethoxybenzoyl chloride in 100 ml. of ethylene dichloride was added slowly with stirring to a cooled mixture containing 7.9 g. of 2,2,4-trimethyl-1,6-hexanediamine, 200 ml. of 10% sodium hydroxide solution and 500 ml. of ethylene dichloride. When no solid separated, the reaction mixture was allowed to stand overnight. The ethylene dichloride layer was separated, washed successively with 1N hydrochloric acid and water, dried over anhydrous magnesium sulfate and evaporated in vacuo to remove ethylene dichloride. The remaining oil solidified after about 48 hours and the resulting solid was recrystallized from isopropyl ether using decolorizing charcoal and dried in vacuo at 60° C. to yield 17.6 g. of N,N'-(2,2,4-trimethylhexamethylene)bis(4-trifluoromethoxybenzamide), m.p. 97°–99° C.

39.
N,N'-(Dithiodiethylene)bis(4-methoxybenzamide), m.p. 136°–138° and 154°–155° C., 16.4 g., was prepared as in Example 1 using a solution of 18.8 g. of 4-methoxybenzoyl chloride in 100 ml. of ethylene dichloride, 11.3 g. of cystamine, [i.e., bis(β-aminoethyl)-disulfide] dihydrochloride, 300 ml. of 10% potassium hydroxide solution, 400 ml. of ethylene dichloride and recrystallization from acetonitrile using decolorizing charcoal.

40.
N,N'-(Dithiodiethylene)bis(4-trifluoromethoxybenzamide), m.p. 150°–151° C., 14.5 g., was prepared as in Example 1 using 33.6 g. of 4-trifluoromethoxybenzoyl chloride in 100 ml. of ethylene dichloride, 11.3 g. of cystamine dihydrochloride, 300 ml. of 10% sodium hydroxide solution, 400 ml. of ethylene dichloride and recrystallization from acetonitrile using decolorizing charcoal.

41.
N,N'-(Diselenodiethylene)bis(4-trifluoromethoxybenzamide), m.p. 140°–142° C., 11.1 g., was prepared as in Example 1 using a solution of 16.6 g. of 4-trifluoromethoxybenzoyl chloride in 50 ml. of ethylene dichloride, 10.0 g. of bis(2-aminoethyl)diselenide, 100 ml. of 10% sodium hydroxide solution, 200 ml. of ethylene dichloride and recrystallization from acetonitrile using decolorizing charcoal.

42.
N,N'-Heptamethylenebis(3,5-dibenzyloxy-4-methoxybenzamide)

To a chilled stirred mixture kept at about 5°–8° C. using an ice bath was added dropwise and simultaneously two solutions, one consisting of 22.5 g. of 3,5-dibenzyloxy-4-methoxybenzoyl chloride in 120 ml. of chloroform and the other containing 4.9 ml. of 35% sodium hydroxide solution and 40 ml. of water. After said solutions had been added, the reaction mixture was stirred while chilled in the ice bath for 1 hour and then stirred for 3 hours at room temperature. The solid was collected, slurried successively in water and n-hexane and dried at 60° C. to yield 20 g. of N,N'-heptamethylenebis(3,5-dibenzyloxy-4-methoxybenzamide), m.p. 206°–209° C.

The above 3,5-dibenzyloxy-4-methoxybenzoyl chloride was prepared as follows: 70 g. of methyl 3,5-dihydroxy-4-methoxybenzoate was dissolved in 650 ml. of dimethylformamide, 157 g. of anhydrous potassium carbonate was added with stirring and the mixture heated to 140° C. To the heated mixture was added with stirring over a period of 75 minutes 132 ml. of benzyl chloride maintaining a reaction temperature of about 140°–145° C. The reaction mixture was stirred for an additional 2 hours at this temperature, allowed to cool to about 110° C. and then the solvent was distilled off under reduced pressure. 500 ml. of ethanol was added to the residue and was distilled off in vacuo; this step was repeated. Then 400 ml. of ethanol plus 300 ml. of 10% aqueous sodium hydroxide solution was added and the mixture was refluxed with stirring for 4 hours and then allowed to stand for 3 days. The solvent was removed in vacuo and one liter of water was added to the residue. The mixture was washed with ether whereupon three layers resulted. The middle oily layer was separated and acidified with acetic acid. The resulting crystalline precipitate was collected, washed well with water and dried in vacuo to yield 119 g. of 3,5-dibenzyloxy-4-methoxybenzoic acid, m.p. 165°–170° C. The 119 g. of 3,5-dibenzyloxy-4-methoxybenzoic acid was mixed with 400 ml. of thionyl chloride, and the mixture was stirred at room temperature for about 10 minutes and then at reflux for 2½ hours and allowed to stand overnight. The excess thionyl chloride was distilled off, the final traces being removed in vacuo. About 250 ml. of dry benzene was added to the residue and was distilled off in vacuo; the benzene treatment was repeated. To the residue was added n-hexane and the mixture was stirred until a well suspended solid resulted. The solid was collected, slurried again with n-hexane and then dried overnight in vacuo to yield 116 g. of 3,5-dibenzyloxy-4-methoxybenzoyl chloride, m.p. 124°–127° C.

43.
N,N'-Heptamethylenebis(3,5-dihydroxy-4-methoxybenzamide)

A mixture containing 14 g. of N,N'-heptamethylenebis(3,5-dibenzyloxy-4-methoxybenzamide), 300 ml. of isopropyl alcohol and 1.2 g. of 10% palladium-on-charcoal was catalytically hydrogenated at 50° C. using 43 p.s.i. of hydrogen and a hydrogenation period of 5 hours. The reaction mixture was filtered and the filtrate concentrated in vacuo to a volume of about 70 ml. The resulting crystalline precipitate was collected, washed with cold isopropyl alcohol and then slurried in 200 ml. of n-hexane for 1 hour to yield 6 g. of N,N'-heptamethylenebis(3,5-dihydroxy-4-methoxybenzamide), m.p. 162°–164° C.

44.
N,N'-(1,1,5-Trimethylheptamethylene)bis(4-trifluoro methoxybenzamide)

m.p. 82°–85° C., 8.57 g., was prepared as in Example 21 using 6.4 g. of 1,1,5-trimethyl-1,7-heptanediamines, 25 ml. of ethylene dichloride, 13.8 g. of anhydrous potassium carbonate, 25 ml. of water, 16.7 g. of 4-trifluoromethoxybenzoyl chloride in 25 ml. of ethylene dichloride and recrystallization from n-hexane.

The above intermediate 1,1,5-trimethyl-1,7-heptanediamine was prepared in two steps as follows: To 100 ml. concentrated sulfuric acid chilled in a bath containing solid carbon dioxide and isopropyl alcohol was added dropwise with stirring 100 ml. of acetonitrile. To the resulting solution kept below 10° C. in an ice bath was added dropwise with stirring over a period of 2 hours a solution containing 46.5 g. of 3,8-dimethyl-6-octenylamine in 30 ml. of acetonitrile. The ice bath was removed and the solution was stirred at room temperature for about 90 minutes. The reaction mixture was poured into a solution containing 160 g. of sodium hydroxide in 1500 ml. of ice and water. The oily layer was separated from the heavier aqueous layer and the aqueous layer was extracted with ether. The oily layer was combined with the ether extract and the resulting solution was washed with brine, dried over anhydrous potassium carbonate, filtered and the filtrate concentrated in vacuo to remove the ether and to leave as a pale yellow, clear viscous oil, 24.4 g. of $N_1$-acetyl-1,1,5-trimethyl-1,7-heptanediamine. A mixture containing 29.4 g. of $N_1$-acetyl-1,1,5-trimethyl-1,7-heptanediamine (5.0 g. obtained from another preparation carried out as above), 15 g. of potassium hydroxide and 130 ml. of ethylene glycol was boiled under reflux with stirring for 48 hours. The clear reaction solution was diluted with an equal volume of water and the mixture was continuously extracted with ether for 24 hours. The ether extract was dried over anhydrous potassium carbonate, filtered and the filtrate heated in vacuo to remove the ether. The remaining oil was distilled under reduced pressure to yield 18.8 g. of 1,1,5-trimethyl-1,7-heptanediamine, b.p. 63°–76° C. at 0.20–0.65 mm.

Following the procedure described in the above examples, e.g., 1, 6, 16, 20, 23 and 29 using the appropriate reactants, preferably a 4-(Q-O)-benzoyl chloride and the appropriate diamine of the formula III, the following compounds are prepared:

45. N,N'-Decamethylenebis(4-trifluoromethoxybenzamide).
46. N,N'-Heptamethylenebis[4-(2-butenyloxy)-benzamide].
47. N,N'-Heptamethylenebis(4-fluoromethoxybenzamide).
48. N,N'-Octamethylenebis(4-difluoromethoxybenzamide).
49. N,N'-Heptamethylenebis(4-dichloromethoxybenzamide).
50. N,N'-Heptamethylenebis[4-(1,1,2,2,2,-pentafluoroethoxy)benzamide].
51. N,N'-Heptamethylenebis[4-(1,1,2,2,-tetrafluorobutoxy)benzamide].
52. N,N'-Heptamethylenebis[4-(2,2-dichlorovinyloxy)benzamide].
53. N,N'-Heptamethylenebis[4-(1,2,2-trifluorovinyloxy)benzamide].
54. N,N'-Heptamethylenebis[4-(3,3-difluoro-2-propenyloxy)benzamide].
55. N,N'-Heptamethylenebis[4-(4-dimethylaminobutoxy)benzamide] by reacting N,N'-heptamethylenebis(4-hydroxybenzamide) with 4-dimethylaminobutyl chloride as in Example 29.
56. N,N'-Heptamethylenebis[4-(3-piperidinopropoxy)-benzamide] by reacting N,N'-heptamethylenebis(4-hydroxybenzamide) with 3-piperidinopropyl chloride as in Example 29.
57. N,N'-Bis(4-trifluoromethoxybenzoyl)-1,7-diaminoheptene-3.
58. N,N'-Bis(4-trifluoromethoxybenzoyl)-2-[2-(3-aminopropyl)cyclohexyl]ethylamine.
59. N,N'-Bis(4-trifluoromethoxybenzoyl)-2-(3-aminocyclohexyl)ethylamine.
60. N,N'-Bis(4-trifluoromethoxybenzoyl)-1,4-bis(2-aminoethyl)benzene.
61. N,N'-Bis(4-methoxybenzoyl)-1,2-bis(3-aminopropyl)cyclopropane.
62. N,N'-(1,1,5-Trimethylheptamethylene)bis(4-methoxybenzamide).
63. N,N'-(1,5-Dimethyloctamethylene)bis(4-trifluoromethoxybenzamide).
64. N,N'-(1,5-Dimethyloctamethylene)bis(4-methoxybenzamide).
65. N,N'-Bis(4-trifluoromethoxybenzoyl)bis(3-aminopropyl)sulfide.
66. N,N'-Bis(4-methoxybenzoyl)bis(3-aminopropyl)-sulfide.
67. N,N'-Bis(4-trifluoromethoxybenzoyl)bis(3-aminopropyl)sulfone.
68. N,N'-Bis(4-methoxybenzoyl)bis(3-aminopropyl)-sulfoxide.
69. N,N'-[Iminobis(trimethylene)]bis(4-methoxybenzamide).
70. N,N'-Heptamethylenebis(4-tribromomethoxybenzamide).
71. N,N'-Heptamethylenebis[4-(1,2,2,2-tetrafluoroethoxy)benzamide].
72. N,N'-Heptamethylenebis[4-(1,1,2,2-tetrafluoroethoxy)benzamide].
73. N,N'-(1-Methylheptamethylene)bis(4-methoxybenzamide).
74. N,N'-(1,5-Dimethylheptamethylene)bis(4-methoxybenzamide).
75. N,N'-Bis(4-methoxybenzoyl)-2-[2-(3-aminobutyl)cyclohexyl]ethylamine.
76. N,N'-Bis(4-methoxybenzoyl)-2-[2-(3-aminobutyl)-1-methylcyclohexyl]ethylamine.
77. N,N'-Bis(4-methoxybenzoyl)-3-(4-amino-4-methylcyclohexyl)butylamine.
78. N,N'-Bis(4-methoxybenzoyl)-3-(4-amino-4-methylcyclohexyl)propylamine.
79. N,N'-Bis(4-methoxybenzoyl)-3-(3-amino-3-methylcyclohexyl)propylamine.
80. N,N'-Bis(4-methoxybenzoyl)-3-(4-aminomethylcyclohexyl)-2-propylamine.
81. N,N'-Bis(4-methoxybenzoyl)-3-(4-aminomethyl-3-methylcyclohexyl)-2-propylamine.

The intermediates used in the preparation of Examples 45–81 are either known or are readily prepared by known methods, e.g., those illustrated hereinabove in Examples 6, 16, 20, 29, 34, 35, 36, 37 and 44.

The following Examples 82–86 inclusive are presented for comparative purposes. The products of these five examples have been found not to have the above-noted applied use characteristics possessed by the compounds of the invention.

82. N,N'-Heptamethylenebis(3-methoxybenzamide)

m.p. 109°–112° C., 8.9 g., was prepared as in Example 1 using 3-methoxybenzoyl chloride (prepared from 38 g. of 3-methoxybenzoic acid as in Example 6) in 200 ml. of ethylene dichloride, 13.0 g. of 1,7-heptanediamine, 250 ml. of 10% aqueous potassium hydroxide solution, 500 ml. of ethylene dichloride and recrystallation from acetonitrile.

83. N,N'-Heptamethylenebis(2-methoxybenzamide), b.p. > 300° C. at 0.11 mm., 16.7 g. as a pale yellow viscous oil, was prepared as in Example 1 using 18.8 g. of 2-methoxybenzoyl chloride in 100 ml. of ethylene dichloride, 6.5 g. of 1,7-heptanediamine, 200 ml. of aqueous potassium hydroxide solution and 500 ml. of ethylene dichloride.

84. N,N'-Heptamethylenebis(4-methylthiobenzamide)

m.p. 181°–182° C., 25.8 g., was prepared as in Example 1 using 4-methylthiobenzoyl chloride (prepared from 31 g. of 4-methylthiobenzoic acid as in Example 6) in 100 ml. of ethylene dichloride, 11.9 g. of 1,7-heptanediamine, 200 ml. of 10% aqueous potassium hydroxide solution, 500 ml. of ethylene dichloride and recrystallization from acetic acid.

85. N,N'-Heptamethylenebis(4-hydroxybenzamide)

A mixture containing 22.0 g. of N,N'-heptamethylenebis(4-acetoxybenzamide) and 200 ml. of 10% aqueous potassium hydroxide solution was refluxed with stirring until a solution was obtained and then continued for an additional 30 minutes. The solution was acidified with 6N hydrochloric acid and the white solid was collected by vacuum filtration. The white solid was dissolved in hot isopropyl alcohol and the hot solution filtered through infusorial earth. The filtrate was heated to boiling and water was added until slight turbidity persisted and the resulting solution was cooled in an ice bath. The separated white crystalline precipitate was collected, washed with water and dried in a vacuum oven at 100° C. to yield 15.5 g. of N,N'-heptamethylenebis(4-hydroxybenzamide), m.p. 180°–181° C.

The above intermediate N,N'-heptamethylenebis(4-acetoxygbenzamide) was prepared as follows: A solution containing 43.6 g. of 4-acetoxybenzoyl chloride in 300 ml. of ethylene dichloride was added gradually with stirring to a cooled mixture containing 13.0 g. of 1,7-heptanediamine, 400 ml. of 10% aqueous potassium hydroxide solution and 900 ml. of ethylene dichloride. The separated white solid was collected, recrystallized from acetonitrile and dried in a vacuum oven at 60° C. to yield 22.1 g. of N,N'-heptamethylenebis(4-acetoxybenzamide), m.p. 181°–182° C.

The intermediate 4-acetoxybenzoyl chloride was prepared as follows: A mixture containing 100 g. of 4-hydroxybenzoic acid and 300 ml. of acetyl chloride was heated on a steam bath for 3½ hours. The excess acetyl chloride was distilled off by heating on the steam bath to yield a solid residue containing 4-acetoxybenzoic acid. To the residue was added 250 ml. of thionyl chloride and the mixture was heated with stirring on a steam bath until the residue dissolved and heating was continued for an additional 15 minutes. The excess thionyl chloride was distilled off in vacuo and the residue was distilled under the vacuum of a water pump to yield as a colorless liquid, 119.2 g. of 4-acetoxybenzoyl chloride, b.p. 172°–174° C. (at 15 mm.).

86. N,N'-Hexamethylenebis(4-hydroxybenzamide)

A mixture containing 214 g. of phenyl 4-hydroxybenzoate, 128.2 g. of 1,6-hexanediamine and 300 ml. of dimethylformamide was refluxed for 3 days and then poured into a mixture containing 2500 ml. of ice and water. The mixture was slightly acidic with 6N of hydrochloric acid and then was stirred and allowed to stand overnight. The resulting tan solid was collected by first decanting most of the water and then by filtration. The solid was recrystallized once from ethanol-water using decolorizing charcoal and then from methanol using decolorizing charcoal, and dired in vacuo at 60° C. to yield 19.1 g. of N,N'-hexamethylenebis(4-hydroxybenzamide), m.p. 220°–222° C.

87. N,N'-Heptamethylenebis(4-pentadeuteroethoxybenzamide)

m.p. 151°–152° C., 3.7 g., was prepared as in Example 1 using 7.6 g. of 4-pentadeuteroethoxybenzoyl chloride (from 6.4 g. of 4-pentadeuteroethoxy benzoic acid as in Example 6) in 10 ml. of ethylene dichloride, 2.0 g. of 1,7-heptanediamine, 20 ml. of 10% aqueous potassium hydroxide solution, 50 ml. of ethylene dichloride and recrystallization twice from ethanol.

The above intermediate 4-pentadeuteroethoxybenzoic acid was prepared as follows: To a stirred mixture containing 8.8 g. of ethyl 4-hydroxybenzoate, 11.0 g. of potassium carbonate, 0.5 g. of potassium iodide and 120 ml. of acetone was added 5.0 g. of pentadeuteroethyl bromide. The reaction mixture was refluxed on a steam bath under a condenser containing solid carbon dioxide for 7½ hours and then allowed to stand overnight. The insoluble solids were filtered off and washed with fresh acetone. The combined filtrate and washings were evaporated to yield 11.3 g. of a liquid. The liquid was taken up in 50 ml. of ether and 50 ml. of water, the resulting mixture shaken well and the layers separated. The aqueous layer was extracted with ether. The combined ether solutions were washed with water and dried over anhydrous sodium sulfate, filtered and evaporated in vacuo to yield 8.5 g. of a colorless liquid. The liquid was dissolved in ether and the ether solution was extracted once with 50 ml. of aqueous potassium hydroxide solution, washed with water, dried over anhydrous sodium sulfate and evaporated in vacuo to yield 7.8 g. of ethyl 4-pentadeuteroethoxybenzoate which was mixed with 50 ml. of 10% potassium hydroxide solution and the resulting mixture heated with stirring on a steam bath for 3¼ hours. The hot reaction mixture was filtered and the filtrate acidified with stirring with 18 ml. of 6N hydrochloric acid. The mixture was diluted with water to facilitate stirring. The separate white precipitate was collected, washed with fresh water and dried in vacuo at 70° C. to yield 6.4 g. of 4-pentadeuteroethoxybenzoic acid, m.p. 198°–200° C.

88. N,N'-(3-Heptene-1,7-diyl)bis(4-methoxybenzamide)

m.p. 141°–143° C., 10.2 g., was prepared as in Example 21 using 8.37 g. of 3-heptene-1,7-diamine, 50 ml. of ethylene dichloride, 18.0 g. of potassium carbonate, 100 ml. of water, 22.4 g. of 4-methoxybenzoyl chloride in 50 ml. ethylene dichloride and recrystallization from methanol.

89. N,N'-Heptamethylenebis(4-tert-butoxybenzamide)

To a solution containing 19.4 g. of 4-tert-butoxybenzoic acid dissolved in 250 ml. tetrahydrofuran was added 16.2 g. 1,1'-carbonyldiimidazole and a resulting mixture was stirred at room temperature for 30 minutes. To the solution was added a solution of 6.5 g. of 1,7-heptanediamine in 50 ml. tetrahydrofuran. The resulting mixture was stirred at room temperature for about 25 hours after which time a small quantity of grey solid was filtered off and washed with fresh tetrahydrofuran. The combined filtrate and washings were evaporated in vacuo and the resulting yellow syrupy residue was taken up in 50 ml. of ether. The ether solution was extracted with two 250 ml. portions of 5% potassium carbonate solution and then washed three times with 100 ml. portions of water. The ether solution was dried over anhydrous sodium sulfate. When the product began to crystallize out of the ether solution when being dried, more ether plus chloroform were added to dissolve the product and the sodium sulfate was filtered off. The ether and chloroform solution was evaporated in vacuo to remove the solvents and the remaining solid was recrystallized from acetonitrile using decolorizing charcoal to yield 11.4 g. N,N'-heptamethylenebis(4-tert-butoxybenzamide), m.p. 135°–136° C.

90. N,N'-Heptamethylenebis(4-difluoromethoxybenzamide)

To a solution containing 15.6 g. of 4-difluoromethoxybenzoic acid was added 13.5 g. of 1,1'-carbonyldiimidazole and the solution was stirred for 45 minutes at room temperature. To the solution was added with stirring 5.4 g. of 1,7-heptanediamine in 50 ml. of tetrahydrofuran. The reaction mixture was stirred at room temperature for 68 hours and then the slightly turbid reaction solution was filtered through a sintered glass funnel and the filtrate was evaporated in vacuo. The remaining white solid residue was dissolved in 400 ml. of chloroform and the chloroform solution was shaken well with 300 ml. of 5% potassium hydroxide solution whereupon a white gelatinous solid separated. The solid was collected, recrystallized from acetonitrile and then recrystallized from benzene to yield 10.6 g. of N,N'-heptamethylenebis(4-difluoromethoxybenzamide), m.p. 138°–139° C.

91. N,N'-Heptamethylenebis(N-methyl-4-trifluoromethoxybenzamide)

To a stirred and cooled solution containing 10.0 g. of N,N'-dimethyl-1,7-heptanediamine, 160 ml. of ethylene dichloride and 96 ml. of water was added simultaneously over a period of 2 hours 23 ml. of 35% aqueous sodium hydroxide solution in 100 ml. of water and 28.3 g. of 4-trifluoromethoxybenzoyl chloride, keeping the temperature of the reaction mixture between 0° and 5° C. using an ice bath. The ice bath was then removed and the reaction mixture was stirred for an additional 2 hours. The organic layer was separated; washed twice with water, once each with dilute hydrochloric acid, dilute sodium bicarbonate solution and water; dried over anhydrous magnesium sulfate; and, concentrated in vacuo to remove the ethylene dichloride. The residual oily material was distilled under reduced pressure at 150° C. and 0.4 mm. to yield, as a yellow viscous oil, 23.3 g. of N,N'-heptamethylenebis(N-methyl-4-trifluoromethoxybenzamide).

The intermediate N,N'-dimethyl-1,7-heptanediamine was prepared as follows: To a mixture containing 24.4 g. of benzaldehyde, 15.0 g. of 1,7-heptanediamine and 115 ml. of benzene was stirred and heated to reflux in a flask fitted with a water separator. After 1 hour at reflux, 3.5 ml. of water had been removed. The benzene was then removed by distilling in vacuo and the residual N,N'-dibenzal-1,7-heptanediamine was dissolved in 150 ml. of acetonitrile. To the acetonitrile solution was added 40.0 g. of methyl iodide in about 50 ml. of acetonitrile and the resulting mixture was stirred and heated to reflux for 2½ hours and then concentrated in vacuo to remove the acetonitrile, thereby leaving the residue containing N,N'-dibenzal-1,7-heptanediamine dimethiodide. The residue was taken up in 250 ml. of 75% aqueous ethanol and the mixture heated for 2 hours. The reaction mixture was allowed to cool and poured into 300 ml. of water and the resulting mixture evaporated in vacuo to remove the ethanol. The remaining water solution was washed with ether and then treated with about two and one-half volumes of 35% aqueous sodium hydroxide solution. The alkaline mixture was extracted twice with ether. The combined ether extracts were dried over anhydrous magnesium sulfate, concentrated in vacuo and distilled at 99°–101° C. at 10 mm. to yield 8.2 g. of N,N'-dimethyl-1,7-heptanediamine. The dihydrochloride of said diamine was prepared by treating a solution of the diamine in absolute ether with an excess of hydrogen chloride in ether and found to melt at 247°–248° C after two recrystallizations from absolute ethanol.

92. N,N'-(cis-3-heptene-1,7-diyl)bis(4-trifluoromethoxybenzamide)

A solution containing 9.86 g. of N,N'-(3-heptyne-1,7-diyl)bis(4-trifluoromethoxybenzamide) in 110 ml. of ethanol and 5.0 ml. of pyridine was hydrogenated in a Parr shaker using 1.0 g. of palladium-on-barium sulfate using an initial pressure of hydrogen of 35.5 psi and taking about 40 minutes. The reaction mixture was filtered to remove the catalyst and the filtrate was concentrated in vacuo to remove the sulfate. The white crystalline solid residue was recrystallized from carbon tetrachloride using a small quantity of methanol to yield, as a white microcrystalline powder after drying in vacuo at 60° C. for about 50 hours, 7.6 g. of N,N'-(cis-3-heptene-1,7-diyl)bis(4-trifluoromethoxybenzamide), m.p. 111°–113° C.

93. N,N'-Nonamethylenebis(4-trifluoromethoxybenzamide)

m.p. 144°–145° C., 12.1 g., was prepared as in Example 1 using 24.6 of 4-trifluoromethoxybenzoyl chloride in 200 ml. ethylene dichloride, 7.9 g. of 1,9-nonanediamine, 60 ml. of 10% aqueous potassium hydroxide solution, 300 ml. of ethylene dichloride and recrystallization from acetonitrile.

94. N,N'-Pentamethylenebis(4-trifluoromethoxybenzamide)

m.p. 154°–155° C., 13.8 g., was prepared as in Example 1 using 24.6 g. of 4-trifluoromethoxybenzoyl chloride in 200 ml. of ethylene dichloride, 5.1 g. of 1,5-pentanediamine, 60 ml. of 10% aqueous potassium hydroxide solution, 300 ml. ethylene dichloride and recrystallization from acetonitrile using decolorizing charcoal.

95. N,N'-Pentamethylenebis(3,4-methylenedioxybenzamide)

m.p. 158°–160°C., 7.9 g., was prepared as in Example 1 using 3,4-methylenedioxybenzoyl chloride (from 16.8 g. of 3,4-methylenedioxybenzoic acid as in Example 6) in 150 ml. of ethylene dichloride, 5.1 g. of 1,5-heptanediamine, 60 ml. of 10% aqueous potassium hydroxide solution, 300 ml. of ethylene dichloride and two recrystallizations from absolute ethanol using decolorizing charcoal during the first recrystallization.

96.
N,N'-Decamethylenebis(4-trifluoromethoxybenzamide)

m.p. 154°–155° C., 13.2 g., was prepared as in Example 1 using 24.8 g. of 4-trifluoromethoxybenzoyl chloride in 150 ml. of ethylene dichloride, 8.6 g. of 1,10-decanediamine, 60 ml. of aqueous potassium hydroxide solution, 350 ml. of ethylene dichloride and recrystallization from ethanol using decolorizing charcoal.

97. N,N'-Decamethylenebis(4-methoxybenzamide)

m.p. 168°–170°C., 11.2 g., was prepared as in Example 1 using 18.8 g. of 4-methoxybenzoyl chloride in 150 ml. of ethylene dichloride, 18.6 g. of 1,10 -decanediamine, 150 ml. of aqueous potassium hydroxide solution, 50 ml. of ethylene dichloride and recrystallization from ethanol using decolorizing charcoal.

98.
N,N'-Heptamethylenebis(N-ethyl-4-methoxybenzamide)

b.p. 240°–250° C. at 0.03 mm. as a viscous oil, 12.1 g., was obtained following the procedure described in Example 1 using 17.0 g. of 4-methoxybenzoyl chloride in 50 ml. of ethylene dichloride, 9.3 g. of N,N'-diethyl-1,7-heptanediamine, 125 ml. of 10% aqueous potassium hydroxide solution and 250 ml. of ethylene dichloride. The product was obtained by successively washing the ethylene dichloride reaction mixture with 100 ml. of 10% aqueous potassium hydroxide solution, 100 ml. of 0.6N hydrochloric acid and water; drying the solution with anhydrous magnesium sulfate and filtering off the drying agent; removing the ethylene dichloride by vacuum distillation; and then distilling the product under reduced pressure.

99.
N,N'-Heptamethylenebis(N-ethyl-4-trifluoromethoxybenzamide)

26.0 g. as a pale yellow liquid, was prepared as in Example 1 using 22.5 g. of 4-trifluoromethoxybenzoyl chloride in 50 ml. of ethylene dichloride, 9.3 g. of N,N'-diethyl-1,7-heptanediamine, 125 ml. of 10% aqueous potassium hydroxide solution, and 250 ml. of ethylene dichloride. The product was isolated as in Example 98 by removing the ethylene dichloride from the washed and dried reaction mixture. The product thus obtained required no further purification by vacuum distillation.

100.
N,N'-Undecamethylenebis(4-methoxybenzamide)

m.p. 150°–151° C., 26.0 g., was prepared as in Example 1 using 37.6 g. of 4-methoxybenzoyl chloride in 100 ml. of ethylene dichloride, 18.6 g. of 1,11-undecanediamine, 300 ml. of 10% aqueous sodium hydroxide solution, 400 ml. of ethylene dichloride and recrystallization from 1500 ml. of acetonitrile using decolorizing charcoal.

101.
N,N'-(3-Heptyne-1,7-diyl)bis(4-trifluoromethoxybenzamide)

To a cooled (<10° C.) mixture containing 11.0 g. of 3-heptyne-1,7-diamine, 27.6 g. of anhydrous potassium carbonate, 100 ml. of ethylene dichloride was added dropwise with stirring a solution containing 36.4 g. of 4-trifluoromethoxybenzoyl fluoride in 50 ml. of ethylene dichloride and stirring of the reaction mixture was continued for 2 hours, the second hour being at room temperature. The precipitate was collected, washed well with water, dried in vacuo at 40° C. and then recrystallized from ethylene dichloride to yield 29.2 g. of white crystalline N,N'-(3-heptyne-1,7-diyl)bis(4-trifluoromethoxybenzamide), m.p. 153°–154° C.

The above intermediate 3-heptyne-1,7-diamine was prepared in four steps starting with 5-chloro-1-pentyne as follows: To a slurry of 0.15 g. of ferric nitrate nonahydrate in 500 ml. of liquid ammonia was added in portions with stirring 3.82 g. of lithium. To the resulting stirred suspension was added dropwise a solution of 51.3 g. of 5-chloro-1-pentyne and 50 ml. of anhydrous ether over a period of 1 hour. The stirring was continued for 30 minutes after the addition had been completed. To the resulting stirred slurry was added 50 ml. of ethylene oxide in one portion and stirring at relux was continued for 8 hours. Two hundred ml. of ether was added followed by an excess of aqueous ammonium chloride solution. The ammonia was allowed to boil off and the layers separated. The distilled aqueous layer was extracted with three 75 ml. portions of ether and the combined ether extracts were washed with brine and dried over anhydrous magnesium sulfate. The ether was removed from the dried solution and the remaining yellow oil was distilled under reduced pressure to yield 35.4 g. of 7-chloro-3-heptyne-1-ol, b.p. 76°–77° C. at 0.05 mm.

A 47.5 g. portion of 4-toluenesulphonyl chloride was added to 26 ml. of pyridine, warming the mixture to 40° C. to effect the solution and the solution was then cooled rapidly to 15° C. To the stirred solution maintained between 15° and 20° C. was added dropwise over a period of 45 minutes with stirring 35.4 g. of 7-chloro-3-heptyne-1-ol. The mixture was then stirred at room temperature for 2 hours and allowed to stand at room temperature for about 18 hours. To the reaction mixture was added 50 ml. of water and the mixture was poured into a mixture of 400 ml. of ice and water. The resulting mixture was extracted with five 100 ml. portions of ether. The combined ether extracts were washed successively with 1% cold hydrochloric acid, 5% aqueous sodium bicarbonate solution, and then dried over anhydrous magnesium sulfate. Removal of the ether by vacuum distillation yielded as a clear colorless oil 64.8 g. of 7-chloro-3-heptyne-1-yl 4-toluenesulphonate.

A mixture of 30.0 g. of the 7-chloro-3-heptyne-1-yl 4-toluenesulphonate, 37.1 g. of potassium phthalimide, 150 ml. of dimethylformamide and 0.5 g. of sodium iodide was stirred at room temperature for 30 hours and then at 105° C. for four hours. The solvent was removed by vacuum distillation and the remaining solid was treated with 250 ml. of water in 150 ml of ether. The mixture was shaken well and the remaining white crystalline solid was collected, washed successively with water and ether, and dried at 60° C. at one-third an atmosphere for 18 hours to yield 33.0 g. of N,N'-(3-heptyne-1,7-diyl)bis(phthalimide), m.p. 110°–115° C. Recrystallization from 95% ethanol yielded 29.2 g. of the product, m.p. 116°–117° C.

A mixture containing 49.0 g. of N,N'-(3-heptyne-1,7-diyl)bis(phthalimide), 17 g. of 85% hydrazine hydrate and 400 ml. of 95% ethanol was boiled under reflux for 3 hours and 15 minutes. The ethanol was distilled off under reduced pressure and 300 ml. of water was added. The aqueous solution was made basic with 10% aqueous hydroxide solution and the resulting basic solution was continuously extracted with methylene dichloride for 3½ hours. The extract was dried over anhydrous potassium carbonate and the solvent removed by distilling in vacuo to yield, as a pale yellow oil, 11.23 g. of 3-heptyne-1,7-diamine.

102.
N,N',N''-(1,4,7-heptamethylene)tris(4-trifluoromethoxybenzamide)

A solution containing 2.1 g. of 1,4,7-heptanetriamine in 25 ml. of ethylene dichloride was added to a solution of 6.9 g. of potassium carbonate in 50 ml. of water. The mixture was stirred and cooled to 5° C. in an ice bath and then was added dropwise thereto to a solution of 9.05 g. of 4-trifluoromethoxybenzoyl fluoride in 25 ml. of ethylene dichloride. The resulting mixture containing a voluminous white precipitate was stirred for 15 minutes at 5° C. and then for 30 minutes at room temperature. The white precipitate was collected, washed well with water, dried at 50° C. for eighteen hours at one-third atmosphere and then recrystallized from 200 ml. of 95% ethanol and dried as before to yield 3.20 g. of N,N',N''-(1,4,7-heptamethylene)tris(4-trifluoromethoxybenzamide), m.p. 234°–235° C.

The above intermediate 1,4,7-heptanetriamine was prepared in two steps as follows: A solution containing 14.3 g. of 1,3,7-tribromoheptane in 20 ml. of dimethylformamide was added dropwise to a stirred, heated (on a steam bath) suspension of 18.5 g. of potassium phthalimide in 50 ml. of dimethylformamide. After the addition had been completed, the reaction mixture was heated on a steam bath with stirring for 3½ hours. The reaction mixture was filtered and the filtrate heated in vacuo to remove most of the dimethylformamide. To the residue was added 100 ml. of water and the mixture was extracted with two 75 ml. portions of chloroform. The combined extracts were washed with brine, dried over anhydrous magnesium sulfate and the chloroform distilled off in vacuo leaving a viscous oil which contained some dimethylformamide. To the oil was added 150 ml. of ethanol and the mixture was heated to boiling and allowed to cool whereupon a white crystalline precipitate separated. The precipitate was collected and dried to yield 11.0 g. of N,N',N''-(1,4,7-heptamethylene) trisphthalimide, m.p. 187°–189° C.

A mixture containing 11.0 g. of N,N',N''-(1,4,7-heptamethylene)trisphthalimide, 4.2 g. of 85% hydrazine hydrate and 100 ml. of 95% ethanol was boiled under reflux for 6 hours. Most of the solvent was distilled off under reduced pressure and the residue was made strongly basic with 10% sodium hydroxide solution. The alkaline solution was continuously extracted with methylene dichloride for 20 hours. The extract was dried over anhydrous potassium carbonate and the solvent distilled off under reduced pressure leaving, as a clear viscous oil, 2.1 g. of 1,3,7-heptanetriamine.

103.
N,N'-Heptamethylenebis[4-(2-methoxyethoxy)benzamide]

To a solution containing 11.7 g. of 4-(2-methoxyethoxy)benzoic acid in 150 ml. of tetrahydrofuran was added 9.8 g. of 1,1'-carbonyldiimidazole and the resulting solution was stirred at room temperature for 45 minutes. To the solution was added 3.9 g. of 1,7-heptanediamine with 25 ml. of tetrahydrofuran. A white gummy material formed instantly, thereby stopping the stirrer. To the mixture was added 50 ml. more of tetrahydrofuran and a gummy material was broken up with a spatula so that stirring could be resumed. The mixture was then stirred for 18 hours at room temperature and then 7.5 g. of a white solid was collected. The filtrate was evaporated to dryness and solid white residue plus the above 7 g. of white solid were taken up in 250 ml. of chloroform and the resulting turbid solution was filtered through a sintered funnel. The filtrate was washed successively with 250 ml. of 5% aqueous potassium bicarbonate solution and 150 ml. of 1N hydrochloric acid. The chloroform solution was then dried over anhydrous potassium carbonate and the chloroform evaporated in vacuo to yield a white solid which was recrystallized from absolute ethanol to yield 7.1 g. of N,N'-heptamethylenebis[4-(2-methoxyethoxy)-benzamide], m.p. 140°–141° C.

The intermediate 4-(2-methoxyethoxy)benzoic acid was prepared as follows: To a solution containing 9.0 g. of silver nitrate in 55 ml. of water was added with stirring a solution containing 2.3 g. of sodium hydroxide in 25 ml. of water. The mixture was stirred for 5 minutes and the precipitated silver oxide was collected, washed well with fresh water and transferred to a 500 ml. round bottom 3-neck flask equipped with a stirrer and covered with 125 ml. of water. To the mixture was added 10 g. of sodium hydroxide and the resulting mixture stirred well. The mixture was warmed on a water bath to about 55°C. and to it was added 10.0 g. of 4-(2-methoxyethoxy)benzaldehyde and the mixture was stirred rapidly for 30 minutes at 50°–60°C. The warm reaction mixture was filtered and the solid washed with a small quantity of boiling water. The combined filtrates were acidified with 6N hydrochloric acid and the resulting white precipitate was collected after stirring the mixture well. The white solid was washed with water, air-dried, recrystallized from 55 ml. of 95% ethanol and air-dried to yield 6.1 g. of 4-(2-methoxyethoxy)benzoic acid, m.p. 153–155°C.

104.
N,N'-[4-Methoxybenzoyliminobis(trimethylene)]-bis(4-methoxybenzamide)

M.p. 117°–119°C., 5.0 g., was prepared as in Example 102 using 4.92 g. of iminobis(propylamine), 100 ml. of ethylene dichloride, 10.4 g. of anhydrous potassium carbonate, 90 ml. of water, 12.8 g. of 4-methoxybenzoyl chloride in 100 ml. of ethylene dichloride and two recrystallizations from chloroformethyl acetate.

105.
N,N'-Dodecamethylenebis(4-trifluoromethoxybenzamide)

M.p. 158°–159° C., 11.3 g., was prepared as in Example 1 using 24.8 g. of 4-trifluoromethoxybenzoyl chloride in 150 ml. of ethylene dichloride, 10.0 g. of 1,12-dodecanediamine, 60 ml. of 10% aqueous potassium hydroxide solution, 350 ml. of ethylene dichloride and recrystallization twice from ethanol and once from isopropyl alcohol.

106.
N,N'-Dodecamethylenebis(4-methoxybenzamide)

m.p. 169°–170°C., 8.6 g., was prepared as in Example 1 using 18.8 g. of 4-methoxybenzoyl chloride in 150 ml. of ethylene dichloride, 10.0 g. of 1,12-dodecanediamine, 60 ml. of 10% aqueous potassium hydroxide solution, 350 ml. of ethylene dichloride, and recrystallization once from acetic acid-water and once from dioxane.

107. N,N'-Undecamethylenebis(4-trifluoromethoxy-benzamide)

m.p. 141.5°–142.5° C., 22.2 g., was prepared as in Example 1 using 24.8 g. of 4-trifluoromethoxybenzoyl chloride in 100 ml. of ethylene dichloride, 9.3 g. of 1,11-undecanediamine, 120 ml. of 10% aqueous potassium hydroxide solution, 400 ml. of ethylene dichloride and recrystallization from acetonitrile.

108. N,N'-Heptamethylenebis(4-cyclopropyloxybenzamide) -

To a solution containing 17.4 g. of 4-cyclopropyloxybenzoic acid in 100 ml. of tetrahydrofuran was added 16.2 g. of 1,1'-carbonyldiimidazole and the resulting solution was stirred at room temperature for 45 minutes. To the stirred solution was then added a solution of 6.4 g. of 1,7-heptanediamine in 75 ml. tetrahydrofuran whereupon a gummy white solid precipitated. In order to facilitate stirring an additional 100 ml. of tetrahydrofuran was added and the mixture was stirred at room temperature for 24 hours. The white solid was collected, washed with tetrahydrofuran and air-dried. The filtrate was evaporated in vacuo to yield a larger quantity of white solid which was dissolved in 300 ml. of chloroform. The above air-dried solid was shaken with 200 ml. of chloroform and an insoluble material was filtered off. The combined chloroform solutions were washed five times with 250 ml. portions of water, dried over anhydrous magnesium sulfate and evaporated in vacuo to yield 27.1 g. of solid. The solid was recrystallized from 750 ml. of acetonitrile, dried in a vacuum oven at 50° C. to yield 16.7 g. of N,N'-heptamethylenebis(4-cyclopropyloxybenzamide), m.p. 158°–159° C.

The intermediate 4-cyclopropyloxybenzoic acid was prepared as follows: A 66.5 g. portion of ethyl 4-hydroxybenzoate was dissolved in 800 ml. of dimethylformamide and to the solution was added 83.0 g. of anhydrous potassium carbonate and 5 g. of potassium iodide. To the resulting stirred suspension was added 60.5 g. of cyclopropyl bromide. The stirred reaction mixture was refluxed for 6 days and the hot reaction mixture was filtered to remove the inorganic solids which were washed well with dimethylformamide. The combined filtrate and dimethylformamide washings were evaporated in vacuo and the remaining liquid-solid residue was taken up in a mixture of 500 ml. of water and 500 ml. of ether. The resulting mixture was shaken well and the layers were separated. The aqueous layer was extracted with 200 ml. of ether. The combined ether solutions were washed successively with two 250 ml. portions of aqueous potassium hydroxide solution, next with 200 ml. 0.5N hydrochloric acid and then with two 100 ml. portions of water. The ether solution was dried over anhydrous magnesium sulfate and the ether removed in vacuo to yield, as an amber liquid, 36.2 g. of ethyl 4-cyclopropyloxy-benzoate.

A mixture containing 33.6 g. of ethyl 4-cyclopropyloxy-benzoate and 330 ml. of 10% aqueous potassium hydroxide solution was stirred and heated on a steam bath for 2½ hours and then allowed to stand overnight at room temperature. The solution was filtered through infusorial earth to remove some turbidity and the filtrate was acidified with 2N hydrochloric acid with stirring. An additional 300–400 ml. of water was added to facilitate stirring. The white solid was collected, washed with a small quantity of water, sucked dry, recrystallized from 185 ml. of acetonitrile and dried in a vacuum oven at 50° C. to yield 17.4 g. of 4-cyclopropyloxybenzoic acid, m.p. 153°–155° C.

109. N,N'-(trans-3-heptene-1,7-diyl)bis(4-trifluoromethoxybenzamide)

m.p. 136°–137° C., 9.9 g., was prepared as in Example 20 using 33.8 g. of 4-trifluoromethoxybenzoyl chloride in 50 ml. of ethylene dichloride, 9.6 g. of trans-3-heptene-1,7-diamine, 21 g. of anhydrous potassium carbonate, 150 ml. of ethylene dichloride, 150 ml. of water and recrystallization from carbon tetrachloride.

The intermediate trans-3-heptene-1,7-diamine was prepared as follows: a 6.9 g. portion of sodium was dissolved with stirring in 200 ml. of liquid ammonia which had been distilled from sodium. To this stirred blue solution was added 12.6 g. of 3-heptyne-1,7-diamine dropwise over a period of 15 minutes. The solution was stirred at −33° C. for 2 hours and the excess sodium was destroyed by careful dropwise addition of concentrated ammonium hydroxide. The ammonia was allowed to distill off overnight. The resulting white solid was dissolved in 20 ml. of concentrated ammonium hydroxide and 80 ml. of water. The solution was extracted with four 50 ml. portions of n-butanol and the combined extracts were dried over two successive portions of anhydrous potassium carbonate. Most of the solvent was removed by fractional distillation at atmospheric pressure and the remaining material was distilled under reduced pressure to yield 9.63 g. of trans-3-heptene-1,7-diamine, b.p. 110°–113° C. at 18 mm.

110. N,N'-Heptamethylenebis(4-cyclobutyloxybenzamide)

A 10.6 g. portion of 4-cyclobutyloxybenzoic acid was dissolved in 95 ml. of tetrahydrofuran at room temperature and to the solution was added 8.9 g. of 1,1'-carbonyldiimidazole. The resulting solution was stirred at room temperature for 45 minutes and to it was then added 3.5 g. of 1,7-heptanediamine in 15 ml. of tetrahydrofuran. A white precipitate separated immediately; the resulting mixture was stirred for 24 hours and then allowed to stand at room temperature for 42 hours. The resulting white solid was collected, rinsed with tetrahydrofuran, air-dried and recrystallized from 400 ml. of ethanol-acetonitrile (70:30). The resulting white solid was dried in a vacuum oven to yield 10.7 g. of N,N'-heptamethylenebis(4-cyclobutyloxybenzamide), m.p. 183°–184° C.

The intermediate 4-cyclobutyloxybenzoic acid was prepared following the procedure described in Example 108 for the preparation of the corresponding 4-cyclopropyloxybenzoic acid using 25 g. of ethyl 4-hydroxybenzamide, 23.1 g. of cyclobutyl bromide, 31 g. of anhydrous potassium carbonate, 2.5 g. of potassium iodide and 300 ml. of dimethylformamide to yield 20.1 g. of ethyl 4-cyclobutyloxybenzoate, which was then hydrolyzed by heating with 200 ml. of 10% aqueous potassium hydroxide solution as in Example 108 to yield 12.7 g. of 4-cyclobutyloxybenzoic acid, m.p.

111.

N,N'-(1-Methylheptamethylene)bis(4-trifluoromethoxybenzamide)

m.p. 137°–138° C., 15.1 g., was prepared as in Example 20 using 18.7 g. of 4-trifluoromethoxybenzoyl fluoride in 50 ml. of ehtylene dichloride, 6.0 g. of 1,7-octanediamine in 100 ml. of ethylene dichloride, 13.8 g. of anhydrous potassium carbonate, and recrystallization from chloroform.

112.

Heptamethylenebis(N-methyl-4-difluoromethoxybenzamide)

A mixture containing 150 ml. of 10% aqueous potassium hydroxide solution, 9.5 g. of N,N'-dimethyl-1,7-heptanediamine and 250 ml. of ethylene dichloride was stirred and cooled in an ice bath. To said stirred mixture was added dropwise with stirring over a period of 70 minutes a solution containing 27.9 g. of 4-difluoromethoxybenzoyl chloride in 50 ml. of ethylene dichloride. The ice bath was then removed and the mixture stirred at room temperature for 18 hours. The layers were separated and the aqueous layer was extracted with a small amount of ethylene dichloride. The combined ehtylene dichloride solutions were washed successively with 50 ml. of 1% aqueous potassium hydroxide solution, 50 ml. of 0.6N hydrochloric acid and two 100 ml. portions of water. The washed ethylene dichloride solution was dried over anhydrous magnesium sulfate and evaporated in vacuo to remove the solvent and thereby yielding, as a viscous amber liquid, 30.3 g. of heptamethylenebis(N-methyl-4-difluoromethoxybenzamide).

113.

N,N'-Heptamethylenebis(N-ethyl-4-difluoromethoxybenzamide)

14.3 g., as a pale yellow viscous syrup, was prepared following the procedure described in Example 112 using 5.5 g. of N,N'-diethyl-1,7-heptanediamine, 75 ml. of 10% aqueous potassium hydroxide solution, 150 ml. of ethylene dichloride and 14.4 g. of 4-difluoromethoxybenzoyl chloride in 30 ml. of ethylene dichloride.

The intermediate N,N'-diethyl-1,7-heptanediamine was prepared as follows: A mixture containing 45.0 g. of 1,7-heptanediamine, 74.2 g. of benzaldehyde and 450 ml. of benzene was refluxed with stirring on a steam bath, and the water which was evolved was collected in a continuous separator. After 1 hour, evolution of the water ceased and a total of 11.6 ml. was collected. The reaction mixture was allowed to stand overnight, a few drops of an antifoam agent (Dow Corning Antifoam Q) was added and the solution was evaporated to remove the solvent. The syrupy residue was taken up in 450 ml. of acetonitrile, 136 g. of ethyl iodide was added and the resulting reaction mixture was refluxed with stirring on a steam bath. After twenty-two hours of refluxing, an additional 50 g. of ethyl iodide was added and refluxing continued for a total of 72 hours. The reaction mixture was evaporated in vacuo. The residue was taken up in 800 ml. of 75% ethanol and the solution refluxed on a steam bath with stirring. After three and one-half hours the reaction mixture was poured into 900 ml. of water and evaporated in vacuo to remove the ethanol. The residual material was cooled in an ice bath, washed twice with ether and then treated carefully with 2000 ml. of 35% aqueous sodium hydroxide solution whereupon the desired diamine separated as an oil. The diamine was extracted from the mixture with two 600 ml. portions of ether. The combined extracts were dried over anhydrous magnesium sulfate and the ether removed by distilling in vacuo. The residual material was distilled under reduced pressure to yield 40.2 g. of N,N'-diethyl-1,7-heptanediamine, b.p. 128–134° C. at 12 mm.

114.

N,N'-Heptamethylenebis(N-n-propyl-4-trifluoromethoxybenzamide)

17.4 g., as a nearly colorless viscous liquid was prepared following the procedure described in Example 112 using 6.4 g. of N,N'-di-n-propyl-1,7-heptanediamine, 90 ml. of 10% aqueous potassium hydroxide solution, 140 ml. of ethylene dichloride and 15.7 g. of 4-trifluoromethyoxybenzoyl chloride in 40 ml. of ethylene dichloride.

The intermediate N,N'-di-n-propyl-1,7-heptanediamine was prepared as follows: To a solution containing 43.5 g. of pyridine in 600 ml. of benzene cooled in an ice bath was added dropwise over a period of 10 minutes 51.0 g. of propionyl chloride. To the resulting stirred and cooled solution was added dropwise over a period of 30 minutes 32.5 g. of 1,7-heptanediamine. After the ice bath was removed, the reaction mixture was stirred at room temperature for 20 hours and then filtered to remove a pale yellow solid. The filtrate was evaporated in vacuo. The residual material was combined with the pale yellow solid and the mixture was shaken well with a mixture of 500 ml. of chloroform, 500 ml. of water and 10 ml. of 12N hydrochloric acid. The layers were separated and the acidic aqueous layer was extracted with four 150 ml. portions of chloroform. The combined chloroform extracts were dried over anhydrous potassium carbonate. When the solid separated from the chloroform solution, an additional 750 ml. of chloroform was added. The mixture was heated to boiling and filtered through a sintered glass funnel. The chloroform solution was evaporated in vacuo and the solid residue was recrystallized from 250 ml. of acetonitrile and dried in a vacuum oven at 50° C. to yield 43.1 g. of heptamethylenebis(propionamide), m.p. 132°–133.5° C.

The bis(propionamide) was reduced as follows: To a stirred and heated (on a steam bath to gentle reflux) mixture kept under an atmosphere of nitrogen and containing 500 ml. of tetrahydrofuran and 11.2 g. of lithium aluminum hydride was added dropwise with stirring over a period of 2.2 hours a hot solution (dropping funnel kept hot by passing steam through a coil of condenser tubing wrapped around funnel) containing 31.5 g. of N,N'-heptamethylenebis(propionamide) in 900 ml. of tetrahydrofuran. The reaction mixture was then refluxed with stirring for 5 hours and then allowed to stand overnight at room temperature. The reaction mixture was reheated to reflux with stirring and to it was added 250 ml. of tetrahydrofuran followed by dropwise addition of 35 ml. of saturated aqueous sodium potassium tartrate over a period of 45 minutes. Stirring and refluxing were continued for three hours; then the mixture was cooled and filtered. The filtrate cake was washed with fresh tetrahydrofuran and the combined filtrates were evaporated in vacuo to yield a solid-liquid mixture. The solid was filtered off and the filtrate was distilled under reduced pressure to yield a 14.2 g. fraction of N,N'-di-n-propyl-1,7-heptanediamine, b.p. 138°– ° C. at 8 mm.

115.
N,N'-Heptamethylenebis(N-n-propy-4-difluoromethoxybenzamide)

17.9 g., as a pale yellow viscous liquid, was prepared as in Example 112 using 7.8 g. of N,N'-di-n-propyl-1,7-heptanediamine, 100 ml. of 10% aqueous potassium hydroxide solution, 160 ml. of ethylene dichloride and 16.5 g. of 4-difluoromethoxybenzoyl chloride in 40 ml. of ethylene dichloride.

116.
N,N'-(trans-3-heptene-1,7-diyl)bis(4-difluoromethoxybenzamide)

A 25.7 g. portion of 4-difluoromethoxybenzoic acid was dissolved in 100 ml. of thionyl chloride and the solution was boiled under reflux for 4½ hours. Most of the excess thionyl chloride was distilled off at atmospheric pressure and the last traces of it were removed by codistillation with ethylene dichloride under reduced pressure leaving 30.2 g. of 4-difluoromethoxybenzoyl chloride. To a stirred and cooled (in an ice bath) mixture of 8.6 g. of trans-3-heptene-1,7-diamine, 100 ml. of ethylene dichloride and 100 ml. of 10% aqueous potassium carbonate solution was added dropwise a solution of 30.2 g. of 4-difluoromethoxybenzoyl chloride in 50 ml. of ethylene dichloride. The reaction mixture was stirred for 1 hour at 5° C., 2 hours at room temperature and then allowed to stand at room temperature over the weekend. The white precipitate was collected, washed with water, dried in vacuo (one-third atmosphere) for 4 hours, recrystallized once from chloroform containing a small amount of methanol, recrystallized a second time from acetonitrile and dried at 50° C. and one-third atmosphere for 22 hours to yield 20.0 g. of N,N'-(trans-3-heptene-1,7-diyl)bis(4-difluoromethoxybenzamide), m.p. 122°–123° C.

117.
N,N'-Diethyl-N,N'-(trans-3-heptene-1,7-diyl)bis(4-trifluoromethoxybenzamide)

A solution containing 20.2 g. of 4-trifluoromethoxybenzoyl chloride in 50 ml. of ethylene dichloride was added dropwise over a period of 2 hours with stirring to a cooled mixture of 8.0 g. of N,N'-diethyl-trans-3-heptene-1,7-diamine, 13.8 g. of anhydrous potassium carbonate, 100 ml. of ethylene dichloride and 100 ml. of water. The reaction mixture was then stirred at room temperature for 3½ hours and the layers separated. The organic layer was shaken with brine, dried over anhydrous potassium carbonate and distilled under reduced pressure to remove the solvent and to leave a pale yellow viscous oil, which still showed a positive test for halogen. The oil was dissolved in 150 ml. of ether; the ether solution was shaken successively with 100 ml. of cold 0.5N hydrochloric acid, 50 ml. of 10% aqueous potassium carbonate solution and saturated brine, and then dried over anhydrous potassium carbonate. Decolorizing charcoal was added during the drying step and the mixture was filtered. The filtrate was distilled in vacuo to remove the solvent. The remaining oil still showed a positive test for halogen and was again dissolved in ether. The ether solution was stirred for 2 hours with an aqueous solution containing 7.5 g. of glycine and 13.8 g. of aqueous potassium carbonate. The layers were separated and the organic layer was shaken with saturated brine and then dried over aqueous potassium carbonate. The solvent was distilled off in vacuo and the remaining viscous oil was dissolved in ether containing 5% methanol and the solution was filtered through a mixture of 25 g. of silica gel and 10 g. of decolorizing charcoal. The solvent was distilled off in vacuo and the remaining oil was stirred for 4½ hours under high vacuum (0.05 mm.) while heating in a water bath kept at 60°–70° C. to yield, as a viscous oil, 18.8 g. of N,N'-diethyl-N,N'-(trans-3-heptene-1,7-diyl)bis(4-trifluoromethoxybenzamide).

The intermediate N,N'-diethyl-trans-3-heptene-1,7-diamine was prepared in two steps as follows: To 100 ml. of pyridine cooled to 0° C. (in an ice-salt bath) was added dropwise with stirring 35.8 g. of acetic anhydride. To the cooled stirred solution was added 18 g. of trans-3-heptene-1,7-diamine in 40 ml. of pyridine at such a rate to keep the temperature less than 10° C.; the addition took about 45 minutes. The reaction mixture was stirred at 5°–10° C. for an additional 30 minutes, was next stirred at room temperature for 6 hours and then allowed to stand at 5° C. overnight. The clear solution was treated with 10 ml. of concentrated ammonium hydroxide with cooling and stirring. The solution was distilled under reduced pressure to remove most of the volatile materials to leave a clear viscous oil. The oil was treated with 100 ml. of water followed by the addition of solid sodium chloride. The mixture was extracted with five 50 ml. portions of chloroform. The combined chloroform extracts were shaken with 100 ml. of saturated brine containing 2 ml. of 6N hydrochloric acid and then dried over anhydrous potassium carbonate. The chloroform was distilled off in vacuo to yield a clear viscous oil which crystallized at room temperature. The solid was purified by dissolving it in chloroform-methanol, treating the solution with decolorizing charcoal and removing the solvents in vacuo to yield, as a clear colorless viscous oil which crystallized at room temperature to yield 28.3 g. of N,N'-(trans-3-heptene-1,7-diyl)bis(acetamide).

To a stirred refluxing solution containing 10.5 g. of lithium aluminum hydroxide in 700 ml. of tetrahydrofuran was added dropwise over a period of 90 minutes a solution containing 28.3 g. of N,N'-(trans-3-heptene-1,7-diyl)bis(acetamide) in 200 ml. of tetrahydrofuran. The reaction mixture was boiled under reflux with stirring for an additional 18 hours. To the reaction mixture was addded dropwise with stirring 40 ml. of a saturated aqueous solution of sodium potassium tartrate and the mixture was boiled for 90 minutes. The mixture was filtered; the filtrate was dried over anhydrous potassium carbonate; and, the filtrate was distilled under reduced pressure to remove the solvents and to leave a pale yellow oil. The oil was dissolved in 100 ml. of tetrahydrofuran and the solution was added dropwise with stirring to a boiling mixture containing 12 g. of lithium aluminum hydride in 250 ml. of tetrahydrofuran. The mixture was boiled with stirring under reflux for 18 hours and the excess hydride was destroyed by slow addition of 40 ml. of a saturated aqueous solution of sodium potassium tartrate. The mixture was boiled with stirring for an additional 90 hours and then filtered. The filtrate was dried over anhydrous potassium carbonate and then distilled under reduced pressure to yield a 15.6 g. fraction of N,N'-diethyl-trans-3-heptene-1,7-diamine, b.p. 62° C. at 0.1 mm.

118.
N-Methyl-N,N'-heptamethylenebis(4-trifluoromethoxybenzamide)

To a mixture chilled in an ice bath and containing 50 ml. of 10% aqueous potassium hydroxide solution, 80 ml. of ethylene dichloride and 2.7 g. of N-methyl-1,7-heptanediamine was added with stirring over a period of 5 minutes a solution containing 8.6 g. of 4-trifluoromethoxybenzoyl chloride in 20 ml. of ethylene dichloride. The reaction mixture was stirred in an ice bath for 15 minutes and then stirred at room temperature for 16 hours. The layers were separated and the ethylene dichloride layer was washed successively with 50 ml. of 1% aqueous potassium hydroxide solution, 50 ml. of 0.6N hydrochloric acid and twice with 50 ml. portions of water. The ethylene dichloride solution was dried over anhydrous magnesium sulfate and evaporated in vacuo to remove the solvent. The residue was heated in a hot (80°–90° C.) water bath for two hours to ensure removal of the ethylene dichloride. There was thus obtained, as a viscous yellow liquid, 9.3 g. of N-methyl-N,N'-heptamethylenebis(4-trifluoromethoxybenzamide).

The intermediate N-methyl-1,7-heptanediamine was prepared as follows: To a stirred mixture cooled to 2°–3° C. and kept under an atmosphere of nitrogen and containing 2.5 g. of lithium aluminum hydride and 70 ml. of ether was added dropwise over a period of 35 minutes a solution containing 8.4 g. of 7-methylaminoheptanonitrile in 30 ml. of ether. The stirred mixture (kept in an ice bath) was then treated dropwise over a period of about 30 minutes with 90 ml. 6N sulfuric acid, keeping the temperature of the reaction between 10°–15° C. The two-phase mixture was filtered and the layers separated. To the aqueous layer was added 250 ml. of 35% aqueous sodium hydroxide solution whereupon there separated an initially copious white solid which dissolved. The mixture was stirred in ice and then extracted with three 100 ml. portions of ether. The combined extracts were dried over anhydrous magnesium sulfate and the ether was distilled off in vacuo to yield 7.4 g. of the residual oil which was shown by gas chromatography to consist of a mixture of the starting 7-methylaminoheptanonitrile and the desired N-methyl-1,7-heptanediamine. To a stirred suspension heated to reflux on a steam bath and kept under an atmosphere of nitrogen and containing 2.1 g. of lithium aluminum hydride and 75 ml. of tetrahydrofuran was added dropwise over a period of 25 minutes a solution containing the above 7.4 g. mixture in 25 ml. of tetrahydrofuran. An additional 100 ml. of tetrahydrofuran was added and the mixture was cooled to room temperature. The lumpy solid which had separated was broken up and the mixture was refluxed with stirring for an additional 90 minutes. The hot suspension was treated with 7 ml. of a saturated solution of potassium sodium tartrate which was added dropwise with rapid stirring over a period of 10 minutes. The hot reaction mixture was stirred for 1 hour and cooled; a grey solid was filtered off and washed with tetrahydrofuran. The combined filtrate and washings were evaporated in vacuo. The remaining pale yellow oil was distilled under reduced pressure to yield a 2.7 g. fraction of N-methyl-1,7-heptanediamine, b.p. 112°–113° C. at 19 mm.

119.
N-Ethyl-N,N'-heptamethylenebis(4-trifluoromethoxybenzamide)

To a stirred mixture kept in an ice bath and containing 115 ml. of 10% aqueous potassium hydroxide solution, 190 ml. of ethylene dichloride and 6.6 g. of N-ethyl-1,7-heptanediamine was added dropwise over a period of 30 minutes a solution containing 19.4 g. of 4-trifluoromethoxybenzoyl chloride in 40 ml. of ethylene dichloride. The ice bath was removed and stirring was continued at room temperature for about 22 hours. The layers were separated and the ethylene dichloride layer was washed successively with 50 ml. of 1% aqueous potassium hydroxide solution, 50 ml. of 0.6N hydrochloric acid and two 75 ml. portions of water. The ethylene dichloride layer was then dried over anhydrous magnesium sulfate and heated in vacuo to remove the ethylene dichloride. The syrupy residue was heated in vacuo in a hot water bath for about 90 minutes to ensure complete removal of the solvent. The remaining viscous product crystallized on standing overnight to yield 16.2 g. of N-ethyl-N,N'-heptamethylenebis(4-trifluoromethoxybenzamide), m.p. 64°–66° C.

The intermediate N-ethyl-1,7-heptanediamine was prepared in two steps as follows: To a stirred mixture kept in an ice bath and containing 7.2 g. of pyridine, 100 ml. of benzene and 9.2 g. of acetic anhydride was added dropwise over a period of a few minutes 10.0 g. of 7-aminoheptanonitrile. The ice bath was removed and the mixture was stirred at room temperature overnight. The reaction mixture was then evaporated to dryness and the residue taken up in a mixture of 60 ml. of water and 60 ml. of chloroform. The mixture was acidified with 6N hydrochloric acid and shaken well. The layers were separated and the aqueous layer was extracted with four 60 ml. portions of chloroform. The combined extracts were dried over anhydrous potassium carbonate and the solvent removed in vacuo to yield, as a viscous yellow liquid, 15.1 g. of 7-acetamidoheptanonitrile.

To 375 ml. of tetrahydrofuran stirred under nitrogen was added 7.2 g. of lithium aluminum hydride. The stirred mixture was heated to gentle reflux and 15.1 g. of 7-acetamidoheptanonitrile in 75 ml. of tetrahydrofuran was added dropwise over a period of 35 minutes. An additional 400 ml. of tetrahydrofuran was added about midway through said addition when a large quantity of grey solid deposited on the walls of the reaction vessel. The reaction mixture was stirred under reflux for an additional 1.75 hours after addition of the nitrile. The reaction mixture was then allowed to stand overnight at room temperature, reheated to reflux and stirred for an additional hour. To the refluxing and stirring mixture was added dropwise over a period of 30 minutes 22 ml. of saturated aqueous sodium potassium tartrate. The reaction mixture was stirred under reflux for 3 more hours and the grey solid filtered off with a sintered glass funnel. The solid was washed with a little tetrahydrofuran. The combined filtrate and washings were evaporated in vacuo to remove the solvent and the residual material was distilled under reduced pressure to yield 7.0 g. of N-ethyl-1,7-heptanediamine, b.p. 98°–103° C. at 5 mm.

120.
N-n-Propyl-N,N'-heptamethylenebis(4-trifluoromethoxybenzamide)

20.8 g., m.p. 74°–75° C., was prepared following the procedure described in Example 119 using 150 ml. of 10% aqueous potassium hydroxide solution, 250 ml. of ethylene dichloride, 9.3 g. of N-n-propyl-1,7-heptanediamine, 27.1 g. of 4-trifluoromethoxybenzoyl chloride in 50 ml. of ethylene dichloride and recrystallization from 50 ml. of acetonitrile.

The intermediate N-n-propyl-1,7-heptanediamine was prepared in two steps following the procedure described in Example 119. There was first obtained, as an amber liquid, 14.4 g. of 7-propionamidoheptanonitrile using 10.0 g. of 7-aminoheptanonitrile, 8.1 g. of propionyl chloride, 6.9 g. of pyridine and 100 ml. of benzene. Next was obtained 9.3 g. of n-propyl-1,7-heptanediamine, b.p. 112°–116° C. at 5 mm., using 8.0 g. of lithium aluminum hydride in 900 ml. of tetrahydrofuran and 18.2 g. of 7-propionamidoheptanonitrile in 100 ml. of tetrahydrofuran.

121.
N,N'-(trans-3,4-epoxyheptene-1,7-diyl)bis(4trifluoromethoxybenzamide)

To a stirred and chilled (3° C., kept in an ice bath) solution containing N,N'-(trans-3-heptene-1,7-diyl)-bis(4-trifluoromethoxybenzamide) dissolved in 300 ml. of chloroform was added in one portion 7.2 g. of 3-chloroperbenzoic acid. The reaction mixture was stirred for an additional 30 minutes at 3°–5° C. and then was allowed to stand at 5° C. for an additional 42 hours. The reaction mixture was then washed successively with three 50 ml. portions of cold 5% aqueous potassium carbonate solution and next with saturated brine, and then it was dried over anhydrous potassium carbonate. The solvent was distilled off in vacuo and the remaining white solid was recrystallized from benzene-ethanol to yield 7.75 g. of N,N'-(trans-3,4-epoxyheptane-1,7-diyl)bis(4-trifluoromethoxybenzamide), m.p. 121°–123° C.

122.
4-Methoxy-4'-trifluoromethoxy-N,N'-heptamethylenebis(benzamide)

A mixture containing 20 g. of N-(7-aminoheptyl)-4-trifluoromethoxybenzamide hydrochloride, 20 ml. of chloroform, 30 ml. of water and 4.8 ml. of 35% aqueous sodium hydroxide solution was stirred at room temperature until said hydrochloride dissolved and the solution was then cooled in an ice bath. To said cooled and stirred solution was added simultaneously a solution containing 9.6 g. of 4-methoxybenzoyl chloride in 50 ml. of chloroform and 5 ml. of 35% aqueous sodium hydroxide solution in 27 ml. of water. The dropwise addition was completed in 40 minutes and the temperature of the reaction mixture was kept below 8° C. The reaction mixture was stirred in the ice bath for 1 additional hour and then at room temperature for 1 more hour. The mixture was kept in a refrigerator overnight. The solid was collected, washed with two 30 ml. portions of water and three 60 ml. portions of n-hexane, then recrystallized from isopropyl alcohol and dried at 60° C. in vacuo to yield 17 g. of 4-methoxy-4'-trifluoromethoxy-N,N'-heptamethylenebis(benzamide), m.p. 158°–160° C.

The intermediate N-(7-aminoheptyl)-4-trifluoromethoxy-benzamide, as its hydrochloride, was prepared in two steps as follows: To a vigorously stirred mixture containing 6 g. of 7-aminoheptanonitrile, 40 ml. of chloroform and 10 ml. of water kept in an ice bath was added simultaneously and dropwise over a period of about 30 minutes a solution containing 11 g. of 4-trifluoromethoxybenzoyl fluoride in 18 ml. of chloroform and 4 ml. of 35% aqueous sodium hydroxide solution diluted to a volume of 25 cc. with water. The reaction mixture was stirred in the ice bath for 1 additional hour and then at room temperature for 1 more hour. The reaction mixture was next cooled, filtered and the layers separated. The chloroform layer was washed with two 50 ml. portions of water and dried over anhydrous calcium sulfate. The chloroform was removed in vacuo to yield 14 g. of oily product, N-(6-cyanohexyl)-4-trifluoromethoxybenzamide, which solidified when cooled in an ice bath, m.p. 25°–30° C.

A mixture containing 12 g. of N-(6-cyanohexyl)-4-trifluoromethoxybenzamide in 100 ml. of ethanol, 8 g. of ammonia and 4 g. of Raney nickel was hydrogenated at approximately 30° C. for a period of 5 hours. The reaction mixture was filtered and the solvent and excess ammonia were removed by heating in vacuo. The residual material was dissolved in 150 ml. of isopropyl alcohol acidified with ethanolic hydrogen chloride and the solution was concentrated in vacuo to about 100 ml. The solution was cooled in an ice bath and the solid that separated was collected, washed with cold isopropyl alcohol and ether, and dried at 60° C. in vacuo to yield 9 g. of N-(7-aminoheptyl)-4-trifluoromethoxybenzamide as its hydrochloride, m.p. 178°–181° C.

123.
4-Trifluoromethoxy-N,N'-heptamethylenebis(benzamide)

To a stirred mixture kept at 2°–5° C. in an ice bath and containing 18 g. of N-(7-aminoheptyl)-4-trifluoromethoxybenzamide hydrochloride, 4.4 ml. of 35% aqueous sodium hydroxide solution, 160 ml. of chloroform and 50 ml. of water was added simultaneously over a period of 40 minutes 4.6 ml. of 35% aqueous potassium hydroxide solution and 7.7 g. of benzoyl chloride. The reaction mixture was then allowed to stand in a refrigerator and the resulting precipitate was collected. The precipitate was extracted with 500 ml. of chloroform. The chloroform solution was washed successively with two 100 ml. portions of dilute hydrochloric acid and two 100 ml. portions of water. The chloroform solution was then dried over anhydrous calcium sulfate and heated in vacuo to remove the chloroform. The solid residue was recrystallized from isopropyl acetate, washed with n-hexane and dried at 60° C. to yield 16 g. of 4-trifluoromethoxy-N,N'-heptamethylenebis(benzamide), m.p. 115°–118° C.

124.
N,N'-Heptamethylenebis(3-fluoro-4-methoxybenzamide)

To a stirred ice-cooled solution containing 125 ml. of 2N aqueous potassium hydroxide solution and 150 ml. of ethylene dichloride was added over a period of fifteen minutes 28.2 g. of 3-fluoro-4-methoxybenzoyl chloride dissolved in 50 ml. of ethylene dichloride whereupon a copious white solid separated. The resulting mixture was stirred in the ice bath for an additional 15 minutes and then stirred at room temperature for 2 hours. The solid was collected, recrystallized from 700 ml. of acetonitrile and dried in vacuo at 50° C. to yield 23.1 g. of N,N'-heptamethylenebis(3-fluoro-4-methoxybenzamide), m.p. 169°–170.5° C.

The intermediate 3-fluoro-4-methoxybenzoyl chloride was prepared as follows: Fifty g. of calcium hypochlorite was dissolved by warming in 200 ml. of water to give a milky solution. A warm solution containing 35 g. of potassium carbonate and 10 g. of potassium hydroxide in 100 ml. of water was added; the resulting mixture was shaken for about 5 minutes and then filtered through a sintered glass funnel. The filtrate cake of calcium carbonate was washed with 40 ml. of water. The combined filtrates were placed in a one liter round bottom flask and stirred while heating on a steam bath to about 55° C. To the stirred solution was added 16.8 g. of 3-fluoro-4-methoxyacetophenone and the stirred suspension was cautiously warmed to 60° C. whereupon an exothermic reaction began. The reaction temperature was allowed to rise to 70° C. and the mixture was cooled to 60° C. using an ice bath; this was repeated several times until the reaction moderated. The stirred reaction mixture was then kept at 60°–70° C. on a steam bath for 30 minutes and then cooled to room temperature with continued stirring. The reaction mixture was filtered and to the filtrate was added 10 g. of sodium metabisulfite in 40 ml. of water to destroy the excess hypochlorite. The mixture was then acidified with 40 ml. of concentrated hydrochloric acid and additional water was added to facilitate stirring due to copious formation of white solid. The mixture was placed in a cold room and the solid was collected, washed with a little water, recrystallized from 150 ml. of acetonitrile and air-dried to yield 12.9 g. of 3-fluoro-4-methoxybenzoic acid, m.p. 211°–212° C.

A mixture containing 25.5 g. of 3-fluoro-4-methoxybenzoic acid and 150 ml. of thionyl chloride was stirred and refluxed gently on a steam bath for 11 hours. After the excess thionyl chloride had been distilled off, 100 ml. of ethylene dichloride was added and distilled off. Another 100 ml. portion of ethylene dichloride was added and distilled off, the last traces being removed using a rotary evaporator for 90 minutes, to yield 28.2 g. of 3-fluoro-4-methoxybenzoyl chloride.

125.
N,N'-Heptamethylenebis(N-phenyl-4-trifluoromethoxybenzamide)

To a stirred cooled mixture containing 5.1 g. of pyridine and 150 ml. of benzene was added dropwise over 5 minutes 14.6 g. of 4-trifluoromethoxybenzoyl chloride followed by dropwise addition over a period of 30 minutes 8.3 g. of N,N'-diphenyl-1,7-heptanediamine in 50 ml. of benzene. The mixture was then stirred at room temperature for one hour and then refluxed on a steam bath for 18 hours. The reaction mixture was filtered and the filtrate was washed successively with 100 ml. 0.5% aqueous potassium hydroxide solution, 100 ml. of 0.6N hydrochloric acid and four times with 50 ml. portions of water. The benzene solution was dried over anhydrous magnesium sulfate and evaporated in vacuo to remove the benzene. The residue was taken up in 150 ml. of chloroform and washed with a solution prepared from 5 g. of glycine, 5 ml. of 10% aqueous potassium hydroxide solution and 100 ml. of water; it was next washed twice with water, stirred with a mixture of anhydrous magnesium sulfate and decolorizing charcoal, and filtered. The filtrate was evaporated in vacuo to remove the solvent and to yield, as a viscous amber liquid, 18.2 g. of N,N'-heptamethylenebis(N-phenyl-4-trifluoromethoxybenzamide).

The intermediate N,N'-diphenyl-1,7-heptanediamine was prepared as follows: A mixture containing 16 g. of pimelic acid and 50 ml. of thionyl chloride in 200 ml. of ethylene dichloride was stirred and refluxed on a steam bath for 2 hours, allowed to stand at room temperature for several hours and then evaporated in vacuo to remove the excess thionyl chloride and the ethylene dichloride. Another 100 ml. portion of ethylene dichloride was added and then distilled off in vacuo. The residue was dissolved in 50 ml. of ethylene dichloride and added dropwise over a period of 10 minutes to a stirred and ice-cooled solution containing 18.6 g. of aniline, 200 ml. of 10% aqueous potassium hydroxide solution and 200 ml. of ethylene dichloride whereupon copious solid separated. An additional 100 ml. of ethylene dichloride was added; the mixture was shaken well for ten minutes and then filtered. The solid was recrystallized from 375 ml. of acetonitrile using decolorizing charcoal and air-dried to yield 20.1 g. of pimelic dianilide, m.p. 159°–161° C.

To a stirred suspension heated to gentle reflux on a steam bath and containing 100 ml. of tetrahydrofuran and 5.1 g. of lithium aluminum hydride was added dropwise over a period of 50 minutes under an atmosphere of nitrogen a solution containing 19.7 g. of pimelic dianilide in 300 ml. of tetrahydrofuran. The reaction mixture was stirred under an atmosphere of nitrogen under reflux for an additional 5 hours and then allowed to stand overnight at room temperature. The reaction mixture was again heated to reflux with stirring and to it was added slowly 16 ml. of saturated sodium potassium tartrate solution. The mixture was refluxed for 2 additional hours, cooled to room temperature and filtered to remove the grey solid. The solid was rinsed with fresh tetrahydrofuran. The combined filtrates were evaporated in vacuo to remove the tetrahydrofuran and the remaining solid residue was recrystallized from 55 ml. of 95% ethanol and air-dried to yield 12.6 g. of N,N'-diphenyl-1,7-heptanediamine, m.p. 52°–54° C.

126.
N-(2-Hydroxyethyl)-N,N'-heptamethylenebis(4-trifluoromethoxybenzamide)

To a stirred and ice-cooled mixture containing 60 ml. of 2N aqueous potassium hydroxide solution and 60 ml. of ethylene dichloride was added a solution of 6.8 g. of N-(2-hydroxyethyl)-1,7-heptanediamine in a small quantity of ethylene dichloride and water. To the resulting stirred and cooled mixture was added dropwise over a period of 20 minutes a solution containing 18.0 g. of 4-trifluoromethoxybenzoyl chloride in 20 ml. of ethylene dichloride. The reaction mixture was stirred for 20 hours at room temperature and the layers then were separated. The aqueous layer was extracted with 50 ml. of ethylene dichloride. The combined ethylene dichloride layer and extract were washed successively with 80 ml. of 0.6N hydrochloric acid and two 50 ml. portions of water. The ethylene dichloride solution was dried over anhydrous magnesium sulfate and evaporated in vacuo to remove the solvent to yield, as a viscous pale yellow liquid, 20.3 g. of N-(2-hydroxyethyl)-N,N'-heptamethylenebis(4-trifluoromethoxybenzamide).

The intermediate N-(2-hydroxyethyl)-1,7-heptanediamine was prepared in two steps as follows: To a stirred and ice-cooled solution containing 650 ml. of benzene and 43.5 g. of pyridine was added dropwise over a period of 30 minutes 75 g. of ethyl oxalyl chloride followed by dropwise addition over a period of 30 minutes 63 g. of 7-amino-heptanonitrile. The reaction mixture was stirred in the ice bath for 3 minutes, next stirred at room temperature for 45 minutes and then allowed to stand overnight at room temperature. The white solid was filtered off and rinsed with fresh benzene. The combined benzene filtrates were washed successively with two 250 ml. portions of 5% aqueous glycine solution containing 25 ml. of 10% aqueous potassium hydroxide solution, a 250 ml. portion of 0.6N hydrochloric acid and two 250 ml. portions of water. The benzene solution was then dried over anhydrous magnesium sulfate and evaporated in vacuo to yield 102.7 g. ethyl N-(6-cyanohexyl)oxamate. A 23.1 g. portion was fractionally distilled at high vacuum for analysis, thereby yielding 14.7 g. of ethyl N-(6-cyanohexyl)oxamate, b.p. 170°–174° C. at 0.05 mm.

To a stirred mixture of 17.4 g. of lithium aluminum hydride and 3200 ml. of tetrahydrofuran kept under nitrogen and heated to reflux was added dropwise over a period of 1 hour 32.9 g. of ethyl N-(6-cyanohexyl)oxamate in 100 ml. of tetrahydrofuran. Heating and stirring were continued for 22 hours and then 1800 ml. of solvent was distilled off. The reaction mixture was refluxed with stirring while 53 ml. of saturated aqueous sodium potassium tartrate was added dropwise over a period of 50 minutes. Stirring and refluxing were continued for an additional 2 hours and the reaction mixture was then allowed to stand at room temperature over the weekend. The grey solid was filtered off and washed with fresh tetrahydrofuran. The combined filtrates were evaporated in vacuo to remove the solvent and the residue was distilled under reduced pressure to yield 27.9 g. of N-(2-hydroxyethyl)-1,7-heptanediamine, b.p. 112°–118° C. at 0.05 mm.

127.
N-(2-Hydroxyethyl)-N,N'-heptamethylenebis(4-difluoromethoxybenzamide)

To a stirred and ice-cooled mixture containing 6.8 g. of N-(2-hydroxyethyl)-1,7-heptanediamine dissolved in 60 ml. of 2N aqueous potassium hydroxide solution and 60 ml. of ethylene dichloride was added dropwise over a period of 25 minutes 16.5 g. of 4-difluoromethoxybenzoyl chloride in 20 ml. of ethylene dichloride. The reaction mixture was stirred in the ice bath for 1 hour and then at room temperature for 20 hours. The layers were separated and the ethylene dichloride layer was washed first with 80 ml. of 0.6N hydrochloric acid and then twice with 60 ml. portions of water; was dried over anhydrous magnesium sulfate; and then was evaporated in vacuo to remove the solvent. The viscous residue was dissolved in 50 ml. of chloroform and purified chromatographically as follows: A 7 cm. diameter chromatography column was packed under 90% ether-10% methanol (v./v.) with 1000 g. of silica gel and the column washed with ether. The product dissolved in 50 ml. of chloroform was placed on the column and the column eluted first with ether, fractions being taken at 250 ml. intervals. The column was eluted with twelve fractions of 100% ether, sixteen fractions of 95% ether-5% methanol and thirteen fractions of 90% ether-10% methanol. Fractions 31–36 inclusive were dissolved in small quantities of chloroform. The chloroform solutions were combined, dried over anhydrous magnesium sulfate, filtered and evaporated in vacuo to yield, as a colorless viscous syrup, 13.6 g. of N-(2-hydroxyethyl)-N,N'-heptamethylenebis(4-difluoromethoxybenzamide).

The compounds of Examples 128-159 are further illustrations of the products which are obtained using the above-described procedures in accordance with this invention:

128. 4-Methyl-4'-trifluoromethoxy-N,N'-heptamethylenebis(benzamide).

129. 4-Ethyl-4'-trifluoromethoxy-N,N'-heptamethylenebis(benzamide).

130. 4-Isopropyl-4'-trifluoromethoxy-N,N'-heptamethylenebis(benzamide).

131. 4-Chloro-4'-trifluoromethoxy-N,N'-heptamethylenebis(benzamide).

132. 4-Fluoro-4'-trifluoromethoxy-N,N'-heptamethylenebis(benzamide).

133. 4-Bromo-4'-trifluoromethoxy-N,N'-heptamethylenebis(benzamide).

134. 4-Benzyloxy-4'-trifluoromethoxy-N,N'-heptamethylenebis(benzamide).

135. 4-Hydroxy-4'-trifluoromethoxy-N,N'-heptamethylenebis(benzamide) by catalytically hydrogenating the compound of Example 134.

136. 3,3'-Difluoro-4-methoxy-4'-trifluoromethoxy-N,N'-heptamethylenebis(benzamide).

137. 4-Dimethylamino-4'-trifluoromethoxy-N,N'-heptamethylenebis(benzamide).

138. N,N'-Heptamethylenebis(2,6-dimethyl-4-trifluoromethoxybenzamide).

139. N,N'-Heptamethylenebis(2,6-dichloro-4-trifluoromethoxybenzamide).

140. 4-Di-n-propylamino-4'-trifluoromethoxy-N,N'-heptamethylenebis(benzamide).

141. 4-Nitro-4'-trifluoromethoxy-N,N'-heptamethylenebis(benzamide).

142. 4-Amino-4'-trifluoromethoxy-N,N'-heptamethylenebis(benzamide) by reducing the 4-nitro compound of Example 141.

143. 4-Trifluoromethyl-4'-trifluoromethoxy-N,N'-heptamethylenebis(benzamide).

144. 4-Trichloromethyl-4'-trifluoromethoxy-N,N'-heptamethylenebis(benzamide).

145. 3,4-Dibenzyloxy-4'-trifluoromethoxy-N,N'-heptamethylenebis(benzamide).

146. 3,4-Dihydroxy-4'-trifluoromethoxy-N,N'-heptamethylenebis(benzamide) by catalytically hydrogenating the compound of Example 145.

147. 3,4,5-Trimethoxy-4'-trifluoromethoxy-N,N'-heptamethylenebis(benzamide).

148. N,N'-Heptamethylenebis(4-methoxy-2-methylbenzamide).

149. N,N'-Heptamethylenebis(4-methoxy-2,6-dimethylbenzamide).

150. N,N'-Heptamethylenebis(3,5-dibenzyloxy-4-trifluoromethoxybenzamide).

151. N,N'-Heptamethylenebis(benzamide)-3,5-dihydroxy-4-(trifluoromethoxybenzamide) by catalytically hydrogenating the compound of Example 150.

152. N,N'-Heptamethylenebis(3-methoxy-4-trifluoromethoxybenzamide).

153. N,N'-Heptamethylenebis[4-(2-pyrrolidinoethoxy)benzamide].

154. N,N'-Heptamethylenebis{4-[3-(2,5-dimethylpyrrolidino)propoxy]benzamide}.

155. N,N'-Heptamethylenebis[4-(2-morpholinoethoxy)benzamide].

156. N,N'-Heptamethylenebis[4-(3-heptamethyleneiminopropoxy)benzamide].

157. N,N'-Heptamethylenebis{4-[2-(2-methylpiperidino)ethoxy]benzamide}.

158. N,N'-Heptamethylenebis{4-[2-(4-methylpiperazino)ethoxy]benzamide}.

159. N,N'-Heptamethylenebis{4-[3-(2,4,6-trimethylpiperidino)propoxy]benzamide}.

The compounds of the invention also can be used in the form of inclusion complexes, e.g., with β-cyclodextrin, as illustrated by Example 160.

160. N,N'-Heptamethylenebis(4-trifluoromethoxybenzamide)-β-cyclodextrin inclusion complex To a solution containing 5.0 g. of N,N'-heptamethylenebis(4-trifluoromethoxybenzamide) in 150 ml. of ethanol was added a solution obtained by dissolving 11.3 g. of β-cyclodextrin in 150 ml. of hot water whereupon a white solid separated. The reaction mixture was refluxed with stirring for 2 hours; another 50 ml. portion of water and another 100 ml. portion of ethanol were added; and, refluxing was continued for an additional 3 hours. The resulting clear solution was then allowed to cool slowly in a cold room. The white solid that separated was collected and dried in vacuo at 40° C. to yield 14.6 g. of N,N'-heptamethylenebis(4-trifluoromethoxybenzamide)-β-cyclodextrin inclusion complex, m.p. 294°–296° C. with decomposition.

The adrenal hypertrophy activity of the compounds of the invention was determined by the following standard test procedure: Adult intact female rats of the Sprague-Dawley strain are housed in individual cages and a daily record is kept of food consumption and cyclic vaginal cellular characteristics. The compound to be tested is dissolved in cottonseed oil or physiological saline and is administered subcutaneously or orally daily, 6 days a week for 2 weeks. Body weights are taken on the 1st, 7th and 15th day of the test. All rats are autopsied on the 15th day within 24 hours after the last injection. The adrenals and other glands are removed and weighed. When desirable, tissues are fixed in Zenkers-formalin. When tested by this procedure, the compounds of the invention were found to produce increases in adrenal weights from about 25% to about 100% at dose levels ranging from about 5 to 100 mg. per kg. per day. The same activity was found in male rats.

The antifertility activity of the compounds of the invention was determined by the following standard test procedure which involves female rats which are medicated prior to, during and after the mating period. The rats are autopsied on the 14th post mating day and the uteri are examined for evidence of pregnancy. The procedural details are as follows: A colony of sexually mature female rats of the Sprague-Dawley strain weighing 200–300 gms. are maintained on routine laboratory care. Daily vaginal smears are examined to record the cyclic characteristics of each rat. A given test is composed of rats which have exhibited a minimum of three coincidental estrus cycles. Three days prior to an expected estrus the rats to be placed on test are grouped, housed individually and placed on medication. The medication consists of a test compound, prepared as a solution or suspension in a suitable vehicle, administered orally via stomach tube once daily for a total of eight medications in a 10 day period (Sunday medications are omitted). One group receives only the vehicle in a like manner to serve as a control. Late in the afternoon of the day preceding the expected estrus a mature proven fertile male is housed with each female overnight. The following morning all males are removed and a vaginal smear of each female is examiner for the presence of spermatozoa as evidence that insemination has occurred. Medication of all inseminated rats is continued through the 7th post insemination day. The rats are autopsied 7 days after the last medication and the uteri removed and examined for evidence of pregnancy. The number of implantation sites, number of resorption sites, total number of fetuses and the number of viable fetuses are recorded. when tested by this procedure, the compounds of the invention were found to have antifertility at dose levels ranging from about 5 to 500 mg. per kg. per day. Compounds of the invention found to have antifertility activity as determined by the above procedure include: N,N'-heptamethylenebis(4-methoxybenzamide), N,N'-heptamethylenebis(4-trifluoromethoxybenzamide), N,N'-heptamethylenebis(4-trideuteromethoxybenzamide), N,N'-heptamethylenebis[4-(2,2,2-trifluoroethoxy)benzamide], N,N'-heptamethylenebis(4-pentadeuteroethoxybenzamide), N,N'-heptamethylenebis(4-tert-butoxybenzamide), N,N'-heptamethylenebis(4-difluoromethoxybenzamide), N,N'-heptamethylenebis(N-methyl-4-trifluoromethoxybenzamide), N,N'-(cis-3-heptene-1,7-diyl)bis(4-trifluoromethoxybenzamide), N,N'-heptamethylenebis(N-ethyl-4-methoxybenzamide), N,N'-heptamethylenebis(N-ethyl-4-trifluoromethoxybenzamide), N,N'-(3-heptyne-1,7-diyl)bis(4-trifluoromethoxybenzamide), N,N'-heptamethylenebis(4-cyclopropyloxybenzamide), heptamethylenebis(N-methyl-4-difluoromethoxybenzamide), N,N'-heptamethylenebis(N-ethyl-4-difluoromethoxybenzamide), N,N'-heptamethylenebis(N-n-propyl-4-trifluoromethoxybenzamide), N-methyl-N,N'-heptamethylenebis(4-trifluoromethoxybenzamide), N-ethyl-N,N'-heptamethylenebis(4-trifluoromethoxybenzamide), N-n-propyl-N,N'-heptamethylenebis(4-trifluoromethoxybenzamide), N,N'-(trans-3,4-epoxyheptane-1,7-diyl)bis(4-trifluoromethoxybenzamide), 4-methoxy-4'-trifluoromethoxy-N,N'-heptamethylenebis(benzamide) and 4-trifluoromethoxy-N,N'-heptamethylenebis(benzamide).

The hypocholesteremic activity of the compounds of formula II was assessed by blood serum cholesterol analysis [Turner et al., Scand. J. Clin. Lab. Investigation 9, 210 (1949)] of male rats receiving the test compound by oral administration as compared with a group of control rats receiving no medication. when tested by this procedure, the compounds were found to reduce serum cholesterol about 20–25% at a dose level of 256 mg. per kg. per day.

The actual determination of the numerical adrenal hypertrophy, antifertility or hypocholesteremic data definitive for a particular compound is readily obtained by standard test procedures, referred to above, by technicians versed in endocrinological test procedures, without any need for any extensive experimentation.

The compounds of the invention can be prepared for use by conventional pharmaceutical procedures: that is, by dissolving or suspending them in a pharmaceutically acceptable vehicle, e.g., aqueous alcohol, glycol, oil solution, or oil-water emulsion, for parenteral or oral administration; or by incorporating them in unit dosage form as tablets or capsules for oral administration either alone or in combination with conventional adjuvants, e.g., calcium carbonate, starch, lactose, talc, magnesium stearate, gum acacia, and the like.

Another aspect of the invention is the compound N-(7-aminoheptyl)-4-trifluoromethoxybenzamide, which as shown hereinabove is useful as an intermediate in the preparation of unsymmetrical compounds of formula I where Q-O is trifluoromethoxy and Y is heptamethylene.

Another aspect of the invention resides in an antifertility composition comprising N,N'-heptamethylenebis(4-methoxybenzamide) as the antifertility ingredient and a pharmaceutical carrier.

Still another aspect of the invention resides in the method of decreasing the incidence of pregnancy in a female animal which comprises administering to said animal N,N'-heptamethylenebis(4-methoxybenzamide).

By a "pharmaceutical carrier", as used hereinabove and in the claims, is meant any pharmaceutically-acceptable vehicle suitable in formulating said antifertility composition, e.g., solid, oily, aqueous and other non-aqueous vehicles. The nature of the pharmaceutical carrier can vary widely, depending upon the intended use and/or route of administration of the composition, for example, N,N'-heptamethylenebis(4-methoxybenzamide) is conveniently administered orally in solid form with the aid of a solid carrier. Thus, the compound can be formulated in unit dosage form as tablets in combination with an adjuvant such as one or more of the following: calcium carbonate, starch, gelatin, talc, magnesium stearate, acacia, and the like, or alternatively, it can be employed in capsule form either alone or admixed with a solid adjuvant. Alternatively, for oral administration, N,N'-heptamethylenebis(4-methoxybenzamide) can be dissolved or suspended in a pharmaceutically-acceptable oil or suspended in an aqueous vehicle.

If the composition is to be administered parenterally by injection, the pharmaceutical carrier can be an aqueous solution of a surfactant of thickening agent in which N,N'-heptamethylenebis(4-methoxybenzamide) in finely divided form produces a stable suspension. Other ingredients may be present if desired, such as sodium chloride to make the solution isotonic, buffers to control pH, germicidal agents, and the like.

Non-aqueous compositions for intramuscular injection can be prepared by dissolving or suspending N,N'-heptamethylenebis(4-methoxybenzamide) in a pharmaceutically-acceptable oil, e.g., peanut oil, cottonseed oil, olive oil, and the like. Other non-aqueous solvents which can be employed are for example absolute ethanol, dodecyl alcohol, dimethylformamide and dimethylacetamide.

I claim:
1. N,N'-heptamethylenebis(4-methoxybenzamide).

* * * * *

UNITED STATES PATENT AND TRADEMARK OFFICE
CERTIFICATE OF CORRECTION

PATENT NO. : 4,009,208
DATED : February 22, 1977
INVENTOR(S) : George Y. Lesher

It is certified that error appears in the above-identified patent and that said Letters Patent are hereby corrected as shown below:

Column 1, line 47 "-CH=, CH-," should read -- -CH=CH-, --.

Column 5, line 64 "$CH_2$less" should read -- $CH_2$ less --.

Column 5, line 66 "N-(CH-Y')-" should read -- N-(CN-Y')- --.

Column 6, line 12 "N-(CH-Y')-" should read -- N-(CN-Y')- --.

Column 6, line 59 "benxoylating" should read -- benzoylating --.

Column 7, line 10 "dicyclohexycarbodiimide" should read -- dicyclohexylcarbodiimide --.

Signed and Sealed this

Seventh Day of June 1977

[SEAL]

Attest:

RUTH C. MASON
Attesting Officer

C. MARSHALL DANN
Commissioner of Patents and Trademarks